(12) United States Patent
Orita et al.

(10) Patent No.: US 7,371,818 B2
(45) Date of Patent: May 13, 2008

(54) POLYPEPTIDE AND DNA THEREOF

(75) Inventors: Satoshi Orita, Osaka (JP); Rie Hayashi, Osaka (JP); Hikaru Sonoda, Toyonaka (JP); Kazuhiko Maekawa, Settsu (JP)

(73) Assignee: Shionogi & Co., Ltd., Osaka (JP)

( * ) Notice: Subject to any disclaimer, the term of this patent is extended or adjusted under 35 U.S.C. 154(b) by 629 days.

(21) Appl. No.: 10/451,417

(22) PCT Filed: Dec. 26, 2001

(86) PCT No.: PCT/JP01/11428

§ 371 (c)(1),
(2), (4) Date: Jun. 23, 2003

(87) PCT Pub. No.: WO02/053592

PCT Pub. Date: Jul. 11, 2002

(65) Prior Publication Data

US 2004/0110921 A1   Jun. 10, 2004

(30) Foreign Application Priority Data

Dec. 28, 2000   (JP) ............................. 2000-401584

(51) Int. Cl.
*C07K 1/00* (2006.01)
(52) U.S. Cl. ..................... 530/350; 435/69.1; 435/7.1
(58) Field of Classification Search ................ None
See application file for complete search history.

(56) References Cited

U.S. PATENT DOCUMENTS

| 5,679,783 | A | 10/1997 | De Robertis et al. | |
|---|---|---|---|---|
| 6,790,660 | B1 * | 9/2004 | Yu et al. | 435/325 |
| 6,852,840 | B2 * | 2/2005 | Yu et al. | 530/350 |

FOREIGN PATENT DOCUMENTS

| EP | 1 213 352 A1 | 6/2002 | |
|---|---|---|---|
| WO | WO 88/00205 A1 | 1/1988 | |
| WO | WO 93/23057 A1 | 11/1993 | |
| WO | WO 95/19429 A2 | 7/1995 | |
| WO | WO 98/21335 A1 | 5/1998 | |
| WO | WO 00/09551 A1 | 2/2000 | |
| WO | WO 01/54477 A2 | 8/2001 | |
| WO | WO 01/54708 A1 * | 8/2001 | |
| WO | WO 01/64885 A1 | 9/2001 | |

OTHER PUBLICATIONS

Chen et al., Growth Factors, 2004, 22(4): 233-241.*
MSNBC News Services, "Mixed results on new cancer drug", Nov. 9, 2000.*
Gura, Science, 1997, 278(7):1041-1042.*
Jain, Scientific American, 1994, pp. 58-65.*
Greenbaum et al., Genome Biology, 2003, vol. 4 (9), pp. 117.1-117.8.*
Alberts et al. Molecular Biology of the Cell, 3rd Edition, 1994, p. 465.*
Mallampalli et al., Biochem. J. 1996, vol. 38, pp. 333-341.*
Fu et al., EMBO journal, 1996, vol. 15, pp. 4392-4401.*
Wozney et al., Prog. Growth Factor Res., vol. 1, No. 4, p. 267-280 (1989).
Piccolo et al., Cell, vol. 86, 589-598, Aug. 23, 1996.
J. Larrain et al., Development, 127, 821-830 (2000).
M. Matsui et al., PNAS, May 9, 2000, vol. 97, No. 10, 5291-5296.
D. M. Duprez et al., Developmental Biology, 174, 448-452 (1996).

* cited by examiner

*Primary Examiner*—Larry R. Helms
*Assistant Examiner*—Hong Sang
(74) *Attorney, Agent, or Firm*—Birch, Stewart, Kolasch & Birch, LLP

(57) ABSTRACT

A novel chordin-like polypeptide is found out in a protein secreted from mesenchymal stem cells. This polypeptide is useful as a cancer marker and a remedy for parotid cancer, lung cancer, esophagus cancer, gastric cancer, duodenal carcinoma, kidney cancer, ureteral cancer, testicular cancer, ovarian cancer, uterine cancer, leukemia, intestinal cancer, colon cancer, rectal cancer, biliary cancer or thyroid cancer cells, etc. Moreover, it is found out that the above polypeptide has an activity of modulating bone differentiation. Thus, this polypeptide is also useful as a bone disease marker and a remedy for bone diseases such as arthritis deformans, rheumatoid arthritis and osteoporosis.

5 Claims, 5 Drawing Sheets

FIG. 2

| Organ | Pathological findings | Age (Age) | Sex | Expression level mRNA/rRNA. | High level expression (Over 0.01) | Expression level Tumor tissue /Normal tissue. | Increase(Over 1.5) Decrease(Under 0.5) |
|---|---|---|---|---|---|---|---|
| Brain | Meningioma | 57 | F | 0.018 | . | 0.81 | |
| | Normal | 28 | M | 0.021 | . | | |
| Parotoid | Adenolymphoma | 35 | M | 0.014 | . | 5.50 | Increase |
| Parotoid | Normal | 62 | M | 0.003 | | | |
| Thyroid gland | Papillary ependymoma | 28 | M | 0.010 | . | 0.64 | |
| | Normal | 35 | F | 0.015 | . | | |
| Lung | Carcinoma adenomatosum | 69 | M | 0.012 | . | 1.60 | Increase |
| | Normal | 27 | M | 0.008 | | | |
| Esophagus | Flat epithelial cancer | 78 | M | 0.029 | . | 2.20 | Increase |
| | Normal | 78 | M | 0.013 | . | | |
| Stomach | Carcinoma adenomatosum | 49 | M | 0.024 | . | 2.80 | Increase |
| | Normal | 58 | M | 0.009 | | | |
| Small intestine | Carcinoma adenomatosum | 43 | F | 0.023 | . | 0.19 | Decrease |
| | Normal | 26 | M | 0.120 | | | |
| Duodenum | | 68 | F | 0.046 | . | 1.68 | Increase |
| | Normal | 30 | M | 0.028 | . | | |
| Rectum | Carcinoma adenomatosum | 19 | M | 0.010 | . | 0.30 | Decrease |
| | Normal | 26 | M | 0.032 | . | | |
| Colon | Carcinoma adenomatosum | 68 | F | 0.020 | . | 0.42 | Decrease |
| | Normal | 68 | F | 0.048 | . | | |
| Kidney | Carcinoma clarocellulare | 62 | M | 0.029 | . | 3.36 | Increase |
| | Normal | 62 | M | 0.009 | | | |
| Adrenal gland | Cancer | 50 | F | 0.011 | . | 0.82 | |
| | Normal | 64 | M | 0.014 | . | | |
| Gall | Carcinoma adenomatosum | 58 | F | 0.007 | | 0.53 | |
| | Normal | 78 | F | 0.014 | . | | |
| Lymph node | non Hodgkin's type lymphoma | 70 | M | 0.004 | | 2.20 | Increase |
| | Normal | 28 | M | 0.002 | | | |
| Spermary | Seminoma | 38 | M | 0.016 | . | 1.99 | Increase |
| | Normal | 71 | M | 0.008 | | | |
| Prostate gland | Carcinoma adenomatosum | 72 | M | 0.015 | . | 1.12 | |
| | Normal | 26 | M | 0.014 | . | | |
| Bladder | Transitional cell carcinoma | 75 | M | 0.016 | . | 1.16 | |
| | Normal | 75 | M | 0.014 | . | | |
| Ureter | Carcinoma transitiocellulare | 78 | F | 0.025 | . | 2.10 | Increase |
| | Normal | 78 | F | 0.012 | . | | |

SEQUENCE LISTING

```
<160> NUMBER OF SEQ ID NOS: 5

<210> SEQ ID NO 1
<211> LENGTH: 2240
<212> TYPE: DNA
<213> ORGANISM: Homo sapiens
<220> FEATURE:
<221> NAME/KEY: CDS
<222> LOCATION: (1)..(2055)
<220> FEATURE:
<221> NAME/KEY: mat_peptide
<222> LOCATION: (91)..(2055)
<220> FEATURE:
<221> NAME/KEY: sig_peptide
<222> LOCATION: (1)..(90)

<400> SEQUENCE: 1 atg ctc tgg ttc tcc ggc gtc ggg gct ctg gct gag cgt tac tgc cgc      48
Met Leu Trp Phe Ser Gly Val Gly Ala Leu Ala Glu Arg Tyr Cys Arg
-30              -25                 -20                 -15 cgc tcg cct ggg att acg tgc tgc gtc ttg ctc cta ctc aat tgc tcg      96
Arg Ser Pro Gly Ile Thr Cys Cys Val Leu Leu Leu Leu Asn Cys Ser
            -10                  -5                  -1   1 ggg gtc ccc atg tct ctg gct tcc tcc ttc ttg aca ggt tct gtt gca     144
Gly Val Pro Met Ser Leu Ala Ser Ser Phe Leu Thr Gly Ser Val Ala
         5                  10                  15 aaa tgt gaa aat gaa ggt gaa gtc ctc cag ata cca ttt atc aca gac     192
Lys Cys Glu Asn Glu Gly Glu Val Leu Gln Ile Pro Phe Ile Thr Asp
     20                  25                  30 aac cct tgc ata atg tgt gtc tgc ttg aac aag gaa gtg aca tgt aag     240
Asn Pro Cys Ile Met Cys Val Cys Leu Asn Lys Glu Val Thr Cys Lys
 35                  40                  45                  50 aga gag aag tgc ccc gtg ctg tcc cga gac tgt gcc ctg gcc atc aag     288
Arg Glu Lys Cys Pro Val Leu Ser Arg Asp Cys Ala Leu Ala Ile Lys
                 55                  60                  65 cag agg gga gcc tgt tgt gaa cag tgc aaa ggt tgc acc tat gaa gga     336
Gln Arg Gly Ala Cys Cys Glu Gln Cys Lys Gly Cys Thr Tyr Glu Gly
             70                  75                  80 aat acc tat aac agc tcc ttc aaa tgg cag agc ccg gct gag cct tgt     384
Asn Thr Tyr Asn Ser Ser Phe Lys Trp Gln Ser Pro Ala Glu Pro Cys
         85                  90                  95 gtt cta cgc cag tgc cag gag ggc gtt gtc aca gag tct ggg gtg cgc     432
Val Leu Arg Gln Cys Gln Glu Gly Val Val Thr Glu Ser Gly Val Arg
     100                 105                 110 tgt gtt gtt cat tgt aaa aac cct ttg gag cat ctg gga atg tgc tgc     480
Cys Val Val His Cys Lys Asn Pro Leu Glu His Leu Gly Met Cys Cys
 115                 120                 125                 130
```

-continued

| | | |
|---|---|---|
| ccc aca tgt cca ggc tgt gtg ttt gag ggt gtg cag tat caa gaa ggg<br>Pro Thr Cys Pro Gly Cys Val Phe Glu Gly Val Gln Tyr Gln Glu Gly<br>            135                     140                     145 | | 528 |
| gag gaa ttt cag cca gaa gga agc aaa tgt acc aag tgt tcc tgc act<br>Glu Glu Phe Gln Pro Glu Gly Ser Lys Cys Thr Lys Cys Ser Cys Thr<br>150                     155                     160 | | 576 |
| gga ggc agg aca caa tgt gtg aga gaa gtc tgt ccc att ctc tcc tgt<br>Gly Gly Arg Thr Gln Cys Val Arg Glu Val Cys Pro Ile Leu Ser Cys<br>            165                     170                     175 | | 624 |
| ccc cag cac ctt agt cac ata ccc cca gga cag tgc tgc ccc aaa tgt<br>Pro Gln His Leu Ser His Ile Pro Pro Gly Gln Cys Cys Pro Lys Cys<br>            180                     185                     190 | | 672 |
| ttg ggt cag agg aaa gtg ttt gac ctc cct ttt ggg agc tgc ctc ttt<br>Leu Gly Gln Arg Lys Val Phe Asp Leu Pro Phe Gly Ser Cys Leu Phe<br>195                     200                     205                     210 | | 720 |
| cga agt gat gtt tat gac aat gga tcc tca ttt ctg tac gat aac tgc<br>Arg Ser Asp Val Tyr Asp Asn Gly Ser Ser Phe Leu Tyr Asp Asn Cys<br>            215                     220                     225 | | 768 |
| aca gct tgt acc tgc agg gac tct act gtg gtt tgc aag agg aag tgc<br>Thr Ala Cys Thr Cys Arg Asp Ser Thr Val Val Cys Lys Arg Lys Cys<br>            230                     235                     240 | | 816 |
| tcc cac cct ggt ggc tgt gac caa ggc cag gag ggc tgt tgt gaa gag<br>Ser His Pro Gly Gly Cys Asp Gln Gly Gln Glu Gly Cys Cys Glu Glu<br>            245                     250                     255 | | 864 |
| tgc ctc cta cga gtg ccc cca gaa gac atc aaa gta tgc aaa ttt ggc<br>Cys Leu Leu Arg Val Pro Pro Glu Asp Ile Lys Val Cys Lys Phe Gly<br>260                     265                     270 | | 912 |
| aac aag att ttc cag gat gga gag atg tgg tcc tct atc aat tgt acc<br>Asn Lys Ile Phe Gln Asp Gly Glu Met Trp Ser Ser Ile Asn Cys Thr<br>275                     280                     285                     290 | | 960 |
| atc tgt gct tgt gtg aaa ggc agg acg gag tgt cgc aat aag cag tgc<br>Ile Cys Ala Cys Val Lys Gly Arg Thr Glu Cys Arg Asn Lys Gln Cys<br>            295                     300                     305 | | 1008 |
| att ccc atc agt agc tgc cca cag ggc aaa att ctc aac aga aaa gga<br>Ile Pro Ile Ser Ser Cys Pro Gln Gly Lys Ile Leu Asn Arg Lys Gly<br>            310                     315                     320 | | 1056 |
| tgc tgt cct att tgc act gaa aag ccc ggc gtt tgc acg gtg ttt gga<br>Cys Cys Pro Ile Cys Thr Glu Lys Pro Gly Val Cys Thr Val Phe Gly<br>            325                     330                     335 | | 1104 |
| gat ccc cac tac aac act ttt gac ggt cgg aca ttt aac ttt cag ggg<br>Asp Pro His Tyr Asn Thr Phe Asp Gly Arg Thr Phe Asn Phe Gln Gly<br>            340                     345                     350 | | 1152 |
| acg tgt cag tac gtt ttg aca aaa gac tgc tcc tcc cct gcc tcg ccc<br>Thr Cys Gln Tyr Val Leu Thr Lys Asp Cys Ser Ser Pro Ala Ser Pro<br>355                     360                     365                     370 | | 1200 |
| ttc cag gtg ctg gtg aag aac gac gcc cgc cgg aca cgc tcc ttc tcg<br>Phe Gln Val Leu Val Lys Asn Asp Ala Arg Arg Thr Arg Ser Phe Ser<br>            375                     380                     385 | | 1248 |
| tgg acc aag tcg gtg gag ctg gtg ctg ggc gag agc agg gtc agc ctg<br>Trp Thr Lys Ser Val Glu Leu Val Leu Gly Glu Ser Arg Val Ser Leu<br>            390                     395                     400 | | 1296 |
| cag cag cac ctc acc gtg cgc tgg aac ggc tcg cgc atc gcg ctc ccc<br>Gln Gln His Leu Thr Val Arg Trp Asn Gly Ser Arg Ile Ala Leu Pro<br>            405                     410                     415 | | 1344 |
| tgc cgc gcg cca cac ttc cac atc gac ctg gat ggc tac ctc ttg aaa<br>Cys Arg Ala Pro His Phe His Ile Asp Leu Asp Gly Tyr Leu Leu Lys<br>            420                     425                     430 | | 1392 |
| gtg acc acc aaa gca ggt ttg gaa ata tct tgg gat gga gac agt ttt<br>Val Thr Thr Lys Ala Gly Leu Glu Ile Ser Trp Asp Gly Asp Ser Phe | | 1440 |

```
                435                 440                 445                 450
gta gaa gtc atg gct gcg ccg cat ctc aag ggc aag ctc tgt ggt ctt         1488
Val Glu Val Met Ala Ala Pro His Leu Lys Gly Lys Leu Cys Gly Leu
                        455                 460                 465 tgt ggc aac tac aat gga cat aaa cgt gat gac tta att ggt gga gat         1536
Cys Gly Asn Tyr Asn Gly His Lys Arg Asp Asp Leu Ile Gly Gly Asp
                470                 475                 480 gga aac ttc aag ttt gat gtg gat gac ttt gct gaa tct tgg agg gtg         1584
Gly Asn Phe Lys Phe Asp Val Asp Asp Phe Ala Glu Ser Trp Arg Val
            485                 490                 495 gag tcc aat gag ttc tgc aac aga cct cag aga aag cca gtg cct gaa         1632
Glu Ser Asn Glu Phe Cys Asn Arg Pro Gln Arg Lys Pro Val Pro Glu
        500                 505                 510 ctg tgt caa ggg aca gtc aag gta aag ctc cgg gcc cat cga gaa tgc         1680
Leu Cys Gln Gly Thr Val Lys Val Lys Leu Arg Ala His Arg Glu Cys
515                 520                 525                 530 caa aag ctc aaa tcc tgg gag ttt cag acc tgc cac tcg act gtg gac         1728
Gln Lys Leu Lys Ser Trp Glu Phe Gln Thr Cys His Ser Thr Val Asp
                    535                 540                 545 tac gcc act ttc tac cgg tcc tgt gtg aca gac atg tgt gaa tgt cca         1776
Tyr Ala Thr Phe Tyr Arg Ser Cys Val Thr Asp Met Cys Glu Cys Pro
                550                 555                 560 gtc cat aaa aac tgt tat tgc gag tca ttt ttg gca tat acc cgg gcc         1824
Val His Lys Asn Cys Tyr Cys Glu Ser Phe Leu Ala Tyr Thr Arg Ala
            565                 570                 575 tgc cag aga gag ggc atc aaa gtc cac tgg gag cct cag cag aat tgt         1872
Cys Gln Arg Glu Gly Ile Lys Val His Trp Glu Pro Gln Gln Asn Cys
        580                 585                 590 gca gcc acc cag tgt aag cat ggt gct gtg tac gat acc tgt ggt ccg         1920
Ala Ala Thr Gln Cys Lys His Gly Ala Val Tyr Asp Thr Cys Gly Pro
595                 600                 605                 610 gga tgt atc aag acc tgt gac aac tgg aat gaa att ggt cca tgc aac         1968
Gly Cys Ile Lys Thr Cys Asp Asn Trp Asn Glu Ile Gly Pro Cys Asn
                    615                 620                 625 aag ccg tgc gtt gct ggg tgc cac tgt cca gca aac ttg gtc ctt cac         2016
Lys Pro Cys Val Ala Gly Cys His Cys Pro Ala Asn Leu Val Leu His
                630                 635                 640 aag gga agg tgc atc aag cca gtc ctt tgt ccc cag cgg tgacctttgt         2065
Lys Gly Arg Cys Ile Lys Pro Val Leu Cys Pro Gln Arg
            645                 650                 655 ttcgatcctt aagactctga aatctggtga ctttgacact gaagcggaag agccaatgaa      2125
ggactgcagt atttgtgtgc ccgattctgt aaacacacac acacagagta tatatgtgta      2185
tatatatata agatatattc aaaaacattg catcatttat atgacctata ggggg           2240

<210> SEQ ID NO 2
<211> LENGTH: 685
<212> TYPE: PRT
<213> ORGANISM: Homo sapiens

<400> SEQUENCE: 2

Met Leu Trp Phe Ser Gly Val Gly Ala Leu Ala Glu Arg Tyr Cys Arg
-30                 -25                 -20                 -15

Arg Ser Pro Gly Ile Thr Cys Cys Val Leu Leu Leu Asn Cys Ser
            -10                 -5                  -1  1

Gly Val Pro Met Ser Leu Ala Ser Ser Phe Leu Thr Gly Ser Val Ala
            5                   10                  15

Lys Cys Glu Asn Glu Gly Glu Val Leu Gln Ile Pro Phe Ile Thr Asp
        20                  25                  30
```

-continued

```
Asn Pro Cys Ile Met Cys Val Cys Leu Asn Lys Glu Val Thr Cys Lys
 35                  40                  45                  50

Arg Glu Lys Cys Pro Val Leu Ser Arg Asp Cys Ala Leu Ala Ile Lys
                 55                  60                  65

Gln Arg Gly Ala Cys Cys Glu Cys Lys Gly Cys Thr Tyr Glu Gly
             70                  75                  80

Asn Thr Tyr Asn Ser Ser Phe Lys Trp Gln Ser Pro Ala Glu Pro Cys
             85                  90                  95

Val Leu Arg Gln Cys Gln Glu Gly Val Val Thr Glu Ser Gly Val Arg
        100                 105                 110

Cys Val Val His Cys Lys Asn Pro Leu Glu His Leu Gly Met Cys Cys
115                 120                 125                 130

Pro Thr Cys Pro Gly Cys Val Phe Glu Gly Val Gln Tyr Gln Glu Gly
                135                 140                 145

Glu Glu Phe Gln Pro Glu Gly Ser Lys Cys Thr Lys Cys Ser Cys Thr
             150                 155                 160

Gly Gly Arg Thr Gln Cys Val Arg Glu Val Cys Pro Ile Leu Ser Cys
        165                 170                 175

Pro Gln His Leu Ser His Ile Pro Pro Gly Gln Cys Cys Pro Lys Cys
    180                 185                 190

Leu Gly Gln Arg Lys Val Phe Asp Leu Pro Phe Gly Ser Cys Leu Phe
195                 200                 205                 210

Arg Ser Asp Val Tyr Asp Asn Gly Ser Ser Phe Leu Tyr Asp Asn Cys
                215                 220                 225

Thr Ala Cys Thr Cys Arg Asp Ser Thr Val Val Cys Lys Arg Lys Cys
             230                 235                 240

Ser His Pro Gly Gly Cys Asp Gln Gly Gln Glu Gly Cys Cys Glu Glu
         245                 250                 255

Cys Leu Leu Arg Val Pro Pro Glu Asp Ile Lys Val Cys Lys Phe Gly
260                 265                 270

Asn Lys Ile Phe Gln Asp Gly Glu Met Trp Ser Ser Ile Asn Cys Thr
275                 280                 285                 290

Ile Cys Ala Cys Val Lys Gly Arg Thr Glu Cys Arg Asn Lys Gln Cys
             295                 300                 305

Ile Pro Ile Ser Ser Cys Pro Gln Gly Lys Ile Leu Asn Arg Lys Gly
             310                 315                 320

Cys Cys Pro Ile Cys Thr Glu Lys Pro Gly Val Cys Thr Val Phe Gly
        325                 330                 335

Asp Pro His Tyr Asn Thr Phe Asp Gly Arg Thr Phe Asn Phe Gln Gly
    340                 345                 350

Thr Cys Gln Tyr Val Leu Thr Lys Asp Cys Ser Ser Pro Ala Ser Pro
355                 360                 365                 370

Phe Gln Val Leu Val Lys Asn Asp Ala Arg Arg Thr Arg Ser Phe Ser
                375                 380                 385

Trp Thr Lys Ser Val Glu Leu Val Leu Gly Glu Ser Arg Val Ser Leu
             390                 395                 400

Gln Gln His Leu Thr Val Arg Trp Asn Gly Ser Arg Ile Ala Leu Pro
         405                 410                 415

Cys Arg Ala Pro His Phe His Ile Asp Leu Asp Gly Tyr Leu Leu Lys
420                 425                 430

Val Thr Thr Lys Ala Gly Leu Glu Ile Ser Trp Asp Gly Asp Ser Phe
435                 440                 445                 450
```

```
Val Glu Val Met Ala Ala Pro His Leu Lys Gly Lys Leu Cys Gly Leu
            455                 460                 465
Cys Gly Asn Tyr Asn Gly His Lys Arg Asp Asp Leu Ile Gly Gly Asp
                470                 475                 480
Gly Asn Phe Lys Phe Asp Val Asp Phe Ala Glu Ser Trp Arg Val
            485                 490                 495
Glu Ser Asn Glu Phe Cys Asn Arg Pro Gln Arg Lys Pro Val Pro Glu
    500                 505                 510
Leu Cys Gln Gly Thr Val Lys Val Lys Leu Arg Ala His Arg Glu Cys
515                 520                 525                 530
Gln Lys Leu Lys Ser Trp Glu Phe Gln Thr Cys His Ser Thr Val Asp
                535                 540                 545
Tyr Ala Thr Phe Tyr Arg Ser Cys Val Thr Asp Met Cys Glu Cys Pro
            550                 555                 560
Val His Lys Asn Cys Tyr Cys Glu Ser Phe Leu Ala Tyr Thr Arg Ala
    565                 570                 575
Cys Gln Arg Glu Gly Ile Lys Val His Trp Glu Pro Gln Gln Asn Cys
580                 585                 590
Ala Ala Thr Gln Cys Lys His Gly Ala Val Tyr Asp Thr Cys Gly Pro
595                 600                 605                 610
Gly Cys Ile Lys Thr Cys Asp Asn Trp Asn Glu Ile Gly Pro Cys Asn
                615                 620                 625
Lys Pro Cys Val Ala Gly Cys His Cys Pro Ala Asn Leu Val Leu His
                630                 635                 640
Lys Gly Arg Cys Ile Lys Pro Val Leu Cys Pro Gln Arg
            645                 650                 655

<210> SEQ ID NO 3
<211> LENGTH: 2066
<212> TYPE: DNA
<213> ORGANISM: Homo sapiens
<220> FEATURE:
<221> NAME/KEY: CDS
<222> LOCATION: (1)..(1881)
<220> FEATURE:
<221> NAME/KEY: mat_peptide
<222> LOCATION: (91)..(1881)
<220> FEATURE:
<221> NAME/KEY: sig_peptide
<222> LOCATION: (1)..(90)

<400> SEQUENCE: 3 atg ctc tgg ttc tcc ggc gtc ggg gct ctg gct gag cgt tac tgc cgc      48
Met Leu Trp Phe Ser Gly Val Gly Ala Leu Ala Glu Arg Tyr Cys Arg
-30             -25                 -20                 -15 cgc tcg cct ggg att acg tgc tgc gtc ttg ctg cta ctc aat tgc tcg      96
Arg Ser Pro Gly Ile Thr Cys Cys Val Leu Leu Leu Leu Asn Cys Ser
            -10                 -5                  -1   1 ggg gtc ccc atg tct ctg gct tcc tcc ttc ttg aca ggt tct gtt gca     144
Gly Val Pro Met Ser Leu Ala Ser Ser Phe Leu Thr Gly Ser Val Ala
        5                   10                  15 aaa tgt gaa aat gaa ggt gaa gtc ctc cag ata cca ttt atc aca gac     192
Lys Cys Glu Asn Glu Gly Glu Val Leu Gln Ile Pro Phe Ile Thr Asp
    20                  25                  30 aac cct tgc ata atg tgt gtc tgc ttg aac aag gaa gtg aca tgt aag     240
Asn Pro Cys Ile Met Cys Val Cys Leu Asn Lys Glu Val Thr Cys Lys
35                  40                  45                  50 aga gag aag tgc ccc gtg ctg tcc cga gac tgt gcc ctg gcc atc aag     288
Arg Glu Lys Cys Pro Val Leu Ser Arg Asp Cys Ala Leu Ala Ile Lys
            55                  60                  65
```

-continued

| | |
|---|---|
| cag agg gga gcc tgt tgt gaa cag tgc aaa ggt tgc acc tat gaa gga<br>Gln Arg Gly Ala Cys Cys Glu Gln Cys Lys Gly Cys Thr Tyr Glu Gly<br>                70                      75                      80 | 336 |
| aat acc tat aac agc tcc ttc aaa tgg cag agc ccg gct gag cct tgt<br>Asn Thr Tyr Asn Ser Ser Phe Lys Trp Gln Ser Pro Ala Glu Pro Cys<br>            85                      90                      95 | 384 |
| gtt cta cgc cag tgc cag gag ggc gtt gtc aca gag tct ggg gtg cgc<br>Val Leu Arg Gln Cys Gln Glu Gly Val Val Thr Glu Ser Gly Val Arg<br>100                      105                    110 | 432 |
| tgt gtt gtt cat tgt aaa aac cct ttg gag cat ctg gga atg tgc tgc<br>Cys Val Val His Cys Lys Asn Pro Leu Glu His Leu Gly Met Cys Cys<br>115                      120                    125                    130 | 480 |
| ccc aca tgt cca ggc tgt gtg ttt gag ggt gtg cag tat caa gaa ggg<br>Pro Thr Cys Pro Gly Cys Val Phe Glu Gly Val Gln Tyr Gln Glu Gly<br>                  135                    140                    145 | 528 |
| gag gaa ttt cag cca gaa gga agc aaa tgt acc aag tgt tcc tgc act<br>Glu Glu Phe Gln Pro Glu Gly Ser Lys Cys Thr Lys Cys Ser Cys Thr<br>                  150                    155                    160 | 576 |
| gga ggc agg aca caa tgt gtg aga gaa gtc tgt ccc att ctc tcc tgt<br>Gly Gly Arg Thr Gln Cys Val Arg Glu Val Cys Pro Ile Leu Ser Cys<br>165                      170                    175 | 624 |
| ccc cag cac ctt agt cac ata ccc cca gga cag tgc tgc ccc aaa tgt<br>Pro Gln His Leu Ser His Ile Pro Pro Gly Gln Cys Cys Pro Lys Cys<br>                  180                    185                    190 | 672 |
| ttg ggt cag agg aaa gtg ttt gac ctc cct ttt ggg agc tgc ctc ttt<br>Leu Gly Gln Arg Lys Val Phe Asp Leu Pro Phe Gly Ser Cys Leu Phe<br>195                      200                    205                    210 | 720 |
| cga agt gat gtt tat gac aat gga tcc tca ttt ctg tac gat aac tgc<br>Arg Ser Asp Val Tyr Asp Asn Gly Ser Ser Phe Leu Tyr Asp Asn Cys<br>                  215                    220                    225 | 768 |
| aca gct tgt acc tgc agg gac tct act gtg gtt tgc aag agg aag tgc<br>Thr Ala Cys Thr Cys Arg Asp Ser Thr Val Val Cys Lys Arg Lys Cys<br>230                      235                    240 | 816 |
| tcc cac cct ggt ggc tgt gac caa ggc cag gag ggc tgt tgt gaa gag<br>Ser His Pro Gly Gly Cys Asp Gln Gly Gln Glu Gly Cys Cys Glu Glu<br>                  245                    250                    255 | 864 |
| tgc ctc cta cga gtg ccc cca gaa gac atc aaa gta tgc aaa ttt ggc<br>Cys Leu Leu Arg Val Pro Pro Glu Asp Ile Lys Val Cys Lys Phe Gly<br>260                      265                    270 | 912 |
| aac aag att ttc cag gat gga gag atg tgg tcc tct atc aat tgt acc<br>Asn Lys Ile Phe Gln Asp Gly Glu Met Trp Ser Ser Ile Asn Cys Thr<br>275                      280                    285                    290 | 960 |
| atc tgt gct tgt gtg aaa ggc agg acg gag tgt cgc aat aag cag tgc<br>Ile Cys Ala Cys Val Lys Gly Arg Thr Glu Cys Arg Asn Lys Gln Cys<br>                  295                    300                    305 | 1008 |
| att ccc atc agt agc tgc cca cag gtg ctg gtg aag aac gac gcc cgc<br>Ile Pro Ile Ser Ser Cys Pro Gln Val Leu Val Lys Asn Asp Ala Arg<br>                  310                    315                    320 | 1056 |
| cgg aca cgc tcc ttc tcg tgg acc aag tcg gtg gag ctg gtg ctg ggc<br>Arg Thr Arg Ser Phe Ser Trp Thr Lys Ser Val Glu Leu Val Leu Gly<br>325                      330                    335 | 1104 |
| gag agc agg gtc agc ctg cag cag cac ctc acc gtg cgc tgg aac ggc<br>Glu Ser Arg Val Ser Leu Gln Gln His Leu Thr Val Arg Trp Asn Gly<br>                  340                    345                    350 | 1152 |
| tcg cgc atc gcg ctc ccc tgc cgc gcg cca cac ttc cac atc gac ctg<br>Ser Arg Ile Ala Leu Pro Cys Arg Ala Pro His Phe His Ile Asp Leu<br>355                      360                    365                    370 | 1200 |
| gat ggc tac ctc ttg aaa gtg acc acc aaa gca ggt ttg gaa ata tct<br>Asp Gly Tyr Leu Leu Lys Val Thr Thr Lys Ala Gly Leu Glu Ile Ser | 1248 |

```
                    375                 380                 385
tgg gat gga gac agt ttt gta gaa gtc atg gct gcg ccg cat ctc aag      1296
Trp Asp Gly Asp Ser Phe Val Glu Val Met Ala Ala Pro His Leu Lys
            390                 395                 400 ggc aag ctc tgt ggt ctt tgt ggc aac tac aat gga cat aaa cgt gat      1344
Gly Lys Leu Cys Gly Leu Cys Gly Asn Tyr Asn Gly His Lys Arg Asp
        405                 410                 415 gac tta att ggt gga gat gga aac ttc aag ttt gat gtg gat gac ttt      1392
Asp Leu Ile Gly Gly Asp Gly Asn Phe Lys Phe Asp Val Asp Asp Phe
    420                 425                 430 gct gaa tct tgg agg gtg gag tcc aat gag ttc tgc aac aga cct cag      1440
Ala Glu Ser Trp Arg Val Glu Ser Asn Glu Phe Cys Asn Arg Pro Gln
435                 440                 445                 450 aga aag cca gtg cct gaa ctg tgt caa ggg aca gtc aag gta aag ctc      1488
Arg Lys Pro Val Pro Glu Leu Cys Gln Gly Thr Val Lys Val Lys Leu
                455                 460                 465 cgg gcc cat cga gaa tgc caa aag ctc aaa tcc tgg gag ttt cag acc      1536
Arg Ala His Arg Glu Cys Gln Lys Leu Lys Ser Trp Glu Phe Gln Thr
            470                 475                 480 tgc cac tcg act gtg gac tac gcc act ttc tac cgg tcc tgt gtg aca      1584
Cys His Ser Thr Val Asp Tyr Ala Thr Phe Tyr Arg Ser Cys Val Thr
        485                 490                 495 gac atg tgt gaa tgt cca gtc cat aaa aac tgt tat gcg agt ca ttt      1632
Asp Met Cys Glu Cys Pro Val His Lys Asn Cys Tyr Cys Glu Ser Phe
    500                 505                 510 ttg gca tat acc cgg gcc tgc aga gag ggc atc aaa gtc cac tgg           1680
Leu Ala Tyr Thr Arg Ala Cys Gln Arg Glu Gly Ile Lys Val His Trp
515                 520                 525                 530 gag cct cag cag aat tgt gca gcc acc cag tgt aag cat ggt gct gtg      1728
Glu Pro Gln Gln Asn Cys Ala Ala Thr Gln Cys Lys His Gly Ala Val
                535                 540                 545 tac gat acc tgt ggt ccg gga tgt atc aag acc tgt gac aac tgg aat      1776
Tyr Asp Thr Cys Gly Pro Gly Cys Ile Lys Thr Cys Asp Asn Trp Asn
            550                 555                 560 gaa att ggt cca tgc aac aag ccg tgc gtt gct ggg tgc cac tgt cca      1824
Glu Ile Gly Pro Cys Asn Lys Pro Cys Val Ala Gly Cys His Cys Pro
        565                 570                 575 gca aac ttg gtc ctt cac aag gga agg tgc atc aag cca gtc ctt tgt      1872
Ala Asn Leu Val Leu His Lys Gly Arg Cys Ile Lys Pro Val Leu Cys
    580                 585                 590 ccc cag cgg tgaccttgt ttcgatcctt aagactctga aatctggtga              1921
Pro Gln Arg
595 ctttgacact gaagcggaag agccaatgaa ggactgcagt atttgtgtgc ccgattctgt    1981 aaacacacac acacagagta tatatgtgta tatatatata agatatattc aaaaacattg    2041 catcatttat atgaactata ggggg                                         2066

<210> SEQ ID NO 4
<211> LENGTH: 627
<212> TYPE: PRT
<213> ORGANISM: Homo sapiens

<400> SEQUENCE: 4

Met Leu Trp Phe Ser Gly Val Gly Ala Leu Ala Glu Arg Tyr Cys Arg
-30                 -25                 -20                 -15

Arg Ser Pro Gly Ile Thr Cys Cys Val Leu Leu Leu Asn Cys Ser
                -10                 -5                  -1   1

Gly Val Pro Met Ser Leu Ala Ser Ser Phe Leu Thr Gly Ser Val Ala
```

-continued

```
                 5                  10                 15
Lys Cys Glu Asn Glu Gly Glu Val Leu Gln Ile Pro Phe Ile Thr Asp
     20                  25                  30

Asn Pro Cys Ile Met Cys Val Cys Leu Asn Lys Glu Val Thr Cys Lys
 35              40                  45                      50

Arg Glu Lys Cys Pro Val Leu Ser Arg Asp Cys Ala Leu Ala Ile Lys
                 55                  60                  65

Gln Arg Gly Ala Cys Cys Glu Gln Cys Lys Gly Cys Thr Tyr Glu Gly
             70                  75                  80

Asn Thr Tyr Asn Ser Ser Phe Lys Trp Gln Ser Pro Ala Glu Pro Cys
         85                  90                  95

Val Leu Arg Gln Cys Gln Glu Gly Val Val Thr Glu Ser Gly Val Arg
     100                 105                 110

Cys Val Val His Cys Lys Asn Pro Leu Glu His Leu Gly Met Cys Cys
115             120                 125                     130

Pro Thr Cys Pro Gly Cys Val Phe Glu Gly Val Gln Tyr Gln Glu Gly
                135                 140                 145

Glu Glu Phe Gln Pro Glu Gly Ser Lys Cys Thr Lys Cys Ser Cys Thr
             150                 155                 160

Gly Gly Arg Thr Gln Cys Val Arg Glu Val Cys Pro Ile Leu Ser Cys
         165                 170                 175

Pro Gln His Leu Ser His Ile Pro Pro Gly Gln Cys Cys Pro Lys Cys
     180                 185                 190

Leu Gly Gln Arg Lys Val Phe Asp Leu Pro Phe Gly Ser Cys Leu Phe
195                 200                 205                 210

Arg Ser Asp Val Tyr Asp Asn Gly Ser Ser Phe Leu Tyr Asp Asn Cys
                215                 220                 225

Thr Ala Cys Thr Cys Arg Asp Ser Thr Val Val Cys Lys Arg Lys Cys
             230                 235                 240

Ser His Pro Gly Gly Cys Asp Gln Gly Gln Glu Gly Cys Cys Glu Glu
         245                 250                 255

Cys Leu Leu Arg Val Pro Pro Glu Asp Ile Lys Val Cys Lys Phe Gly
     260                 265                 270

Asn Lys Ile Phe Gln Asp Gly Glu Met Trp Ser Ser Ile Asn Cys Thr
275                 280                 285                 290

Ile Cys Ala Cys Val Lys Gly Arg Thr Glu Cys Arg Asn Lys Gln Cys
                295                 300                 305

Ile Pro Ile Ser Ser Cys Pro Gln Val Leu Val Lys Asn Asp Ala Arg
             310                 315                 320

Arg Thr Arg Ser Phe Ser Trp Thr Lys Ser Val Glu Leu Val Leu Gly
         325                 330                 335

Glu Ser Arg Val Ser Leu Gln Gln His Leu Thr Val Arg Trp Asn Gly
     340                 345                 350

Ser Arg Ile Ala Leu Pro Cys Arg Ala Pro His Phe His Ile Asp Leu
355                 360                 365                 370

Asp Gly Tyr Leu Leu Lys Val Thr Thr Lys Ala Gly Leu Glu Ile Ser
                375                 380                 385

Trp Asp Gly Asp Ser Phe Val Glu Val Met Ala Ala Pro His Leu Lys
             390                 395                 400

Gly Lys Leu Cys Gly Leu Cys Gly Asn Tyr Asn Gly His Lys Arg Asp
         405                 410                 415

Asp Leu Ile Gly Gly Asp Gly Asn Phe Lys Phe Asp Val Asp Asp Phe
     420                 425                 430
```

-continued

```
Ala Glu Ser Trp Arg Val Glu Ser Asn Glu Phe Cys Asn Arg Pro Gln
435                 440                 445                 450

Arg Lys Pro Val Pro Glu Leu Cys Gln Gly Thr Val Lys Val Lys Leu
                455                 460                 465

Arg Ala His Arg Glu Cys Gln Lys Leu Lys Ser Trp Glu Phe Gln Thr
            470                 475                 480

Cys His Ser Thr Val Asp Tyr Ala Thr Phe Tyr Arg Ser Cys Val Thr
        485                 490                 495

Asp Met Cys Glu Cys Pro Val His Lys Asn Cys Tyr Cys Glu Ser Phe
    500                 505                 510

Leu Ala Tyr Thr Arg Ala Cys Gln Arg Glu Gly Ile Lys Val His Trp
515                 520                 525                 530

Glu Pro Gln Gln Asn Cys Ala Ala Thr Gln Cys Lys His Gly Ala Val
                535                 540                 545

Tyr Asp Thr Cys Gly Pro Gly Cys Ile Lys Thr Cys Asp Asn Trp Asn
            550                 555                 560

Glu Ile Gly Pro Cys Asn Lys Pro Cys Val Ala Gly Cys His Cys Pro
        565                 570                 575

Ala Asn Leu Val Leu His Lys Gly Arg Cys Ile Lys Pro Val Leu Cys
    580                 585                 590

Pro Gln Arg
595

<210> SEQ ID NO 5
<211> LENGTH: 1006
<212> TYPE: DNA
<213> ORGANISM: Homo sapiens

<400> SEQUENCE: 5
tatttgaact aggaaatgcc ggctgagagc ccttttcgac tgtgagctgc ggcagctgag     60
cagaggcggc ggcgcgggac ctgcagtcgc cagggattcc ctccaggtga cgatgctctg    120
gttctccggc gtcgggctc tggctgagcg ttactgccgc cgctcgcctg ggattacgtg    180
ctgcgtcttg ctgctactca attgctcggg ggtccccatg tctctggctt cctccttctt    240
gacaggttct gttgcaaaat gtgaaaatga aggtgaagtc ctccagatac catttatcac    300
agacaaccct tgcataatgt gtgtctgctt gaacaaggaa gtgacatgta agagagagaa    360
gtgccccgtg ctgtcccgag actgtgccct ggccatcaag cagagggag cctgttgtga    420 acagtgcaaa ggttgcacct atgaaggaaa tacctataac agctccttca atggcagag    480 cccggctgag ccttgtgttc tacgccagtg ccaggagggc gttgtcacag agtctggggt    540
gcgctgtgtt gttcattgta aaacccttt ggagcatctg gaatgtgct gccccacatg    600 tccaggctgt gtgtttgagg gtgtgcagta tcaagaaggg aggaatttc agccagaagg    660 aagcaaatgt accaagtgtt cctgcactgg aggcaggaca caatgtgtga gagaagtctg    720
tcccattctc tcctgtcccc agcaccttag tcacataccc caggacagt gctgcccaa    780 atgtttgggt cagaggaaag tgtttgacct ccctttttggg agctgcctct ttcgaagtga    840
tgtttatgac aatggatcct catttctgta cgataactgc acagcttgta cctgcaggga    900
ctctactgtg gtttgcaaga ggaagtgctc ccaccctggt ggctgtgacc aaggccagga    960
gggctgttgt gaagagtgcc tcctacgagt gcccccagaa gacatc              1006
```

POLYPEPTIDE AND DNA THEREOF

This application is the national phase under 35 U.S.C. § 371 of PCT International Application No. PCT/JP01/11428 which has an International filing date of Dec. 26, 2001, which designated the United States of America.

TECHNICAL FIELD

The present invention relates to a novel polypeptide having a structure similar to chordin which is involved in inhibition of bone cell differentiation, a polynucleotide encoding the polypeptide, a complementary polynucleotide to the polynucleotide, a vector including the polynucleotide, transformant transformed by the vector, an antibody recognizing the polypeptide, a ligand recognizing the polypeptide, a screening method of a compound using the polypeptide, use as a marker of cancer and bone diseases of the polypeptide and the polynucleotide.

BACKGROUND ART

Osteogenesis, a phenomenon of bone regeneration by osteoblasts, is important in maintaining vertebrate organisms. Many factors involved in osteogenesis are known, such as hormones, such as estrogen, calcitonine and parathyroid hormone (PHT), growth factors, such as osteogenetic factor (BMP: Bone Morphogenetic Protein), and medicines, such as activated vitamin D, a calcium drug, and vitamin K. BMP, a group of diffusible factors belonging to the TGF-β family, has been reported to include about 20 kinds of genes (Molecular Medicine, 37, 634 (2000)). Among them, BMP-2 and BMP-4 have been reported by many to possess a modulatory activity of bone differentiation. On the other hand, BMP, expected as a novel remedy for bone-related diseases, is the only cytokine possessing an activity as a signal of ectopic formation. BMP is thought to be useful for osteogenesis (endochondral ossification), which takes place in a repair reaction at a bone fracture or a bone defect, and which is caused by displacement of chondroid by neonatal bone (Developmental Biology, 174, 448 (1996). Journal of Bone and Mineral Research, 9(5), 651 (1994)). It has also been reported that mesenchymal stem cells have pluripotency and can differentiate to adipocytes, cartilage cells or osteoblasts, depending on the culture condition (Science, 284, 143 (1999)) and that the bone differentiation of mesenchymal stem cells is induced by BMP-2 (Journal of Cell Biology, 113, 681 (1991)). Thus, BMP, which induces bone differentiation, is thought to be associated with osteogenesis-related diseases, such as rheumatoid arthritis, osteoarthritis or osteoporosis. Actually, gene therapy using BMP has been attempted (Molecular Medicine, 37, 709 (2000)). However, the mechanisms of action of BMP in these diseases have not been analyzed in detail, although a solution is desired.

BMP has been found to induce differentiation from a fibroblast to an osteoblast via the receptor, by using an alkaline phosphatase activity as an indicator (Biochemical and Biophysical Research Communications, 172, 295 (1990)). Further, it has been found that the activity of BMP is suppressed by chordin, a protein secreted by Spemann organizer tissue (Nature, 382, 595 (1996)) and that chordin does not bind to the BMP receptor, but directly binds to BMP and acts as an antagonist (Cell, 86, 589 (1996)). Recently, chordin has been determined to have four repeated structures (CR1 to CR4) which have a signal peptide at the amino terminal end and contain an abundance of Cysteine and bind to BMP via the characteristic structure (motif) (Development, 127, 821 (2000)). And, Kielin has been reported to be a secreted protein having a high homology with chordin (Proceedings of the National Academy of Sciences, 97(10), 5291-5296 (2000)). At present, chordin-like proteins other than Kielin are suggested to exist. But, the reality is not clear and the discovery of novel proteins has been sought for the analysis of the mechanism of action of BMP.

On the other hand, cancer may be present in most tissues of the body. Many oncogenes, cancer target genes, and anti-oncogenes have been discovered, and mechanisms of human carcinogenesis are continuing to being discovered on a specified gene level. However, mechanisms of carcinogenesis have not been completely clarified. There is a possibility of unknown genes being involved therein. For example, causative genes have not yet been identified in parotid cancer, esophagus cancer, duodenal carcinoma, ureteral cancer, testicle cancer, ovarian cancer, uterine cancer, intestinal cancer, rectal cancer, biliary cancer and thyroid cancer. An identification of novel genes concerning pathogenesis of cancer and diagnostic methods using the gene have been desired for these diseases. Since cancer cells commonly proliferate in a dedifferentiated state, there are many trials that use factors and pharmaceutical compositions for modulating differentiation of carcinoma cells as anticancer agents. However, such trials can not suppress all cancers. Thus, novel factors and pharmaceutical compositions possessing activity of modulating differentiation are desired.

DISCLOSURE OF INVENTION

The present invention provides a novel polypeptide and polynucleotide useful for diagnostics of cancer and bone diseases, as well as a remedy for cancer and bone diseases with the polypeptide and an inhibitory agent thereof.

The present inventors have intensively attempted to isolate a novel gene concerning the inhibition of differentiation of bone cells, and have found a novel gene encoding chordin-like novel polypeptide (C0783). Further investigation revealed that the gene expression of this novel gene was increased or decreased in a variety of organs having cancer, and as a result, the polypeptide and polynucleotide thus discovered were useful as a cancer marker. Further studies revealed that the expression of the gene is raised, upon the differentiation from stem cells to bone, and that the protein bound with BMP to exhibit an activity as a control factor of bone differentiation, whereby the present invention has been achieved.

That is to say, the present invention relates to:

(1) A polypeptide or salt thereof comprising an amino acid sequence consisting of #1 (Cys) to #655 (Arg) of the SEQ ID NO: 2;

(2) A polypeptide or salt thereof as described in (1), comprising an amino acid sequence consisting of #30 (Met) to #655 (Arg) of the SEQ ID NO: 2;

(3) A polypeptide or salt thereof comprising an amino acid sequence consisting of #1 (Cys) to #597 (Arg) of the SEQ ID NO: 4;

(4) A polypeptide or salt thereof, comprising an amino acid sequence consisting of #30 (Met) to #597 (Arg) of the SEQ ID NO: 4;

(5) A polypeptide or salt thereof, which comprises an amino acid sequence having at least one mutation selected from deletion, displacement and insertion of one or more amino acids in the amino acid sequence as described in any one of (1) to (4) and which is a cancer marker or has a BMP-binding activity;

(6) A polypeptide as described in any one of (1) to (5), which is used as a cancer marker, a bone diseases marker, a cancer remedy or a remedy for bone diseases;

(7) A polynucleotide comprising a nucleotide sequence encoding the polypeptide, described in any one of (1) to (6);

(8) A polynucleotide as described in (7), comprising the nucleotide sequence consisting of #91 (T) to #2055 (G) of the SEQ ID NO: 1;

(9) A polynucleotide as described in (7), comprising the nucleotide sequence consisting of #1 (A) to #2055 (G) of the SEQ ID NO: 1;

(10) A polynucleotide as described in (7), comprising the nucleotide sequence consisting of #91 (T) to #1881 (G) of the SEQ ID NO: 3;

(11) A polynucleotide as described in (7), comprising the nucleotide sequence consisting of #1 (A) to #1881 (G) of the SEQ ID NO: 3;

(12) A polynucleotide that hybridizes to a polynucleotide as described in any one of (7) to (11) under stringent conditions and that encodes a polypeptide which is a cancer marker or has a BMP-binding activity;

(13) A polynucleotide comprising a complementary nucleotide sequence to a polynucleotide as described in any one of (7) to (12);

(14) A polynucleotide as described in any one of (7) to (11) or (13), which is used as a cancer maker, a bone diseases marker, a cancer remedy or a remedy for bone diseases;

(15) A polynucleotide selected from the group consisting of an oligonucleotide having a sequence identical to that of a continuous stretch of 5 to 60 bases in the nucleotide sequence as described in the SEQ ID NO: 1 or 3, a complementary sequence to the oligonucleotide and their oligonucleotide derivatives;

(16) A recombinant vector comprising the polynucleotide as described in any one of (7) to (13);

(17) A transformant, which is transformed with the recombinant vector as described in (16);

(18) A method of preparation of a polypeptide or salt thereof, comprising a process of culturing the transformant as described in (17) and a process of recovering the produced polypeptide as described in any one of (1) to (5) from the culture;

(19) An antibody which specifically recognizes the polypeptide as described in any one of (1) to (5);

(20) A method of detection or quantitative analysis of the polypeptide as described in any one of (1) to (5), which comprises using the antibody as described in (19) and the following processes;
  (a) a step of contacting a polypeptide with the antibody; and
  (b) a step of detecting a binding between the polypeptide and the antibody;

(21) A method of detection of cancer or bone disease relating to the polypeptide as described in any one of (1) to (5), which comprises using the antibody as described in (19);

(22) A kit for diagnosis of cancer or bone diseases, comprising the antibody as described in (19);

(23) A method of detection or quantitative analysis of mRNA of the polypeptide as described in any one of (1) to (5), which comprises using the polynucleotide as described in any one of (7) to (13) or (15) and the following processes;
  (a) a process of contacting an mRNA with the polypeptide, and
  (b) a process of detecting the binding between the mRNA and the polypeptide;

(24) A method of detection of cancer or bone diseases relating to the polypeptide as described in any one of (1) to (5), which comprises using the method as described in (23);

(25) A method for measuring the quantity of the expression of gene encoding the polypeptide as described in any one of (1) to (5), which comprises using the method as described in (23);

(26) A method for inhibiting the transcription of DNA or the translation of mRNA encoding the polypeptide as described in any one of (1) to (5), which comprises using the polynucleotide as described in any one of (7) to (13) or (15);

(27) A kit for diagnosis of cancer or bone diseases, comprising the polynucleotide as described in any one of (7) to (13) or (15);

(28) A method for screening binding of an agent to the polypeptide as described in any one of (1) to (5), comprising the following processes,
  (a) a process of contacting a test agent with the polypeptide as described in any one of (1) to (5), and
  (b) a process of detecting binding between the test agent and the polypeptide;

(29) A kit for screening binding of an agent to the polypeptide as described in any one of (1) to (5), comprising:

(30) A binding agent which is obtainable by the method for screening a binding agent as described in (28);

(31) A binding agent as described in (30) which is BMP-2 and BMP-4;

(32) A method for screening for an agent that modulates a binding activity between a binding agent as described in any one of (30) or (31) and a polypeptide as described in any one of (1) to (5), comprising the following processes,
  (a) a process of contacting the polypeptide as described in any one of (1) to (5) with the binding agent as described in any one of (30) and (31) in the presence or absence of a test agent, and
  (b) a process of comparing both of the binding activities of the polypeptide with the binding agent in the presence and absence of the test agent;

(33) A kit for screening for an agent that modulates binding activity, comprising the polypeptide as described in any one of (1) to (5) and the binding agent as described in any one of (30) and (31);

(34) An agent for modulating a binding activity which is obtainable by the screening method as described in (32);

(35) A method of screening for an agent that modulates the expression of the polypeptide as described in any one of (1) to (5), comprising the following processes;
  (a) a process of contacting a cell which expresses the polypeptide as described in any one of (1) to (5) with a test agent, and
  (b) a process of detecting the change of expression of the polypeptide by the method as described in any one of (20) or (23);

(36) A kit for screening for an agent that modulates the expression of the polypeptide as described in any one of (1) to (5) by the method as described in (35);

(37) An agent for modulating the expression of the polypeptide, which is obtainable by the screening method as described in (35);

(38) A non-human knockout animal, wherein a DNA encoding the polypeptide as described in any one of (1) to (5) is deficient or transformed;

(39) A non-human transgenic animal, wherein a DNA encoding the polypeptide as described in any one of (1) to (5) is deficient or transformed;

(40) A pharmaceutical composition containing the antibody as described in (19), the binding agent as described in (39), the agent for modulating a binding activity as described in (34) or the agent for modulating the expression as described in (37).

The polypeptide of this invention comprises "a polypeptide or salt thereof containing an amino acid sequence represented by #1 (Cys) to #655 (Arg) as described in the SEQ ID NO: 2" and "a polypeptide or salt as described in (1), comprising the amino acid sequence represented by #-30 (Met) to #655 (Arg) as described in the SEQ ID NO: 2". And the polypeptide comprises "a polypeptide or salt thereof containing an amino acid sequence represented by #1 (Cys) to #597 (Arg) is described in the SEQ ID NO: 4" and "a polypeptide or salt thereof comprising the amino acid sequence represented by #-30 (Met) to #597 (Arg) as described in the SEQ ID NO: 4", wherein 58 amino acid residues from #315 (Gly) to #372 (Gln) are deficient in the amino acid sequence as described in the SEQ ID NO: 2.

The term "salt" herein used includes a physiologically acceptable salt of acid or base, preferably a physiologically acceptable acid-addition salt. The salt is exemplified by a salt with a mineral acid such as hydrochloric acid, phosphoric acid, hydrobromic acid, and sulfuric acid, or a salt with an organic acid such as acetic acid, formic acid, proprionic acid, fumaric acid, maleic acid, succinic acid, tartaric acid, citric acid, malic acid, oxalic acid, benzoic acid, methanesulfonic acid, and benzenesulfonic acid.

The polypeptide of the present invention comprises "a polypeptide or salt thereof, which comprises an amino acid sequence having at least one mutation, selected from deletion, displacement and insertion of one or more amino acids in the amino acid sequence as described in (1) to (4) and which is a cancer marker and/or has an BMP-binding activity". The term "one or more amino acid" herein used means a number of amino acids which can be deleted, displaced and inserted by site-directed mutagenesis, and 50 or less residues, preferably 30 or less residues, more preferably 20 or less and most preferably 10 or less amino acid residues. Furthermore, the polypeptide of the present invention has biological activities even when having a mutation such as deletion, displacement or insertion and works as a cancer marker or has a BMP-binding activity. The polypeptide has 60% or more homology with the amino acid sequence represented by the SEQ ID NO: 2 or 4, preferably 80% or more homology and more preferably 95% or more homology.

The term "cancer marker" used in the present invention refers to an agent that can be used to detect cancer cells or cancer tissues, and that is useful when the expression of an mRNA or a protein increases or decreases in cancer diseases. Examples of "cancer" include Parotid cancer, lung cancer, esophagus cancer, gastric cancer, duodenal carcinoma, kidney cancer, liver cancer, liver cancer, bladder cancer, ureteral cancer, testicular cancer, ovarian cancer, uterine cancer, mammary cancer, leukemia, colon cancer, intestinal cancer, colon cancer, rectal cancer, biliary cancer and thyroid cancer. The cancer marker includes any substance capable of detecting cancer, such as a polynucleotide, a polypeptide or an antibody of the present invention.

The term "cancer remedy" used in the present invention refers to an agent for treating cancer diseases. Since the expression of the polypeptide of the present invention increases or decreases in various kinds of cancer cells or cancer tissues, the polypeptide, polynucleotide or antibody of the present invention is useful for treating various kinds of cancers.

The term "BMP-binding activity" used in the present invention refers to possessing an ability to bind to various BMPs, preferably to BMP-2 or BMP-4.

The polypeptide of the present invention binds to BMP, and BMP induces bone differentiation. Therefore, the polypeptide, polynucleotide and antibody are thought to be useful as a bone disease marker or a remedy for bone diseases which are considered to be related to BMP, e.g. rheumatoid arthritis, osteoarthritis, and osteoporosis. The term "bone disease marker" used herein refers to an agent for detecting bone diseases. When the expression of an mRNA or a protein increases or decreases, the agent may be useful as "a cancer marker". The "bone disease marker" includes any substance capable of detecting a bone disease, such as a polypeptide, a polynucleotide, an antibody, or the like in the present invention. The "remedy for bone diseases" is an agent for treating a bone disease. Since the polypeptide of the present invention binds to BMP, a polypeptide, a polynucleotide, an antibody or the like of the present invention is useful for treating a bone disease which is considered to be related to BMP, e.g. rheumatoid arthritis, osteoarthritis, and osteoporosis, by modulating an induced activity of bone differentiation.

The polynucleotide of the present invention is a DNA encoding the polypeptide of the present invention and is exemplified by "a polynucleotide, comprising the nucleotide sequence represented by #91 (T) to #2055 (G) of the SEQ ID NO: 1", "a polynucleotide, comprising the base sequence represented by #1 (A) to #2055 (G) of the SEQ ID NO: 1", "a polynucleotide, comprising the base sequence represented by #91 (T) to #1881 (G) of the SEQ ID NO: 3" or "a polynucleotide, comprising the base sequence represented by #1 (A) to #1881 (G) of the SEQ ID NO: 3". The polynucleotide in the present invention comprises "a polynucleotide", which hybridizes with the polynucleotide in the present invention under stringent conditions and encodes the polypeptide, which is a cancer marker and/or has a BMP-binding activity. Preferably, the polynucleotide of the present invention is "a polynucleotide" comprising the nucleotide sequence represented by #91 (T) to #2055 (G) of the SEQ ID NO: 1" or "a polynucleotide, comprising the nucleotide sequence represented by #91 (T) to #1881 (G) of the SEQ ID NO: 3".

The term "polynucleotide hybridizing under stringent conditions" used herein refers to the polynucleotide obtainable by well-known methods in this field, such as the colony hybridization method, the plaque hybridization method and the southern blotting method, using a polynucleotide as a probe, which is selected from the polynucleotides in the present invention. Concretely, it means the polynucleotide which can be identified by washing with a solution of 0.1 to 2 times concentrated SSC (Saline Sodium Citrate; 150 mM NaCl, 15 mM sodium citrate) after the hybridization is carried out in 0.7 to 1.0 M of NaCl at 65° C. using an immobilized membrane of polynucleotide obtained from a colony or a plaque. The hybridization can be carried out according to the method described in Molecular Cloning: A Laboratory Manual, Second Edition (1989) (Cold Spring Harbor Laboratory Press), Current Protocols in Molecular Biology (1994) (Wiley-Interscience), DNA Cloning 1: Core Techniques, A Practical Approach, Second Edition (1995) (Oxford University Press). Preferably, the sequence comprised of only adenine (A) or thymine (T) is excluded from the hybridizing sequence under a stringent condition.

The term "hybridizing polynucleotide" used in the present invention refers to a polynucleotide which can be hybridized to another polynucleotide under the above hybridizing condition. Such a polynucleotide can be exemplified by one which has at least 60% homology with the base sequence of the DNA encoding a polypeptide having an amino acid sequence represented by SEQ ID NO: 1 or 3, preferably 80% or more homology and more preferably 95% or more homology. The homology is shown by a score obtained by, for example, BLAST, a search program using an algorithm developed by Altschul et al. (The Journal of Molecular Biology, 215, 403-410 (1990)).

The polynucleotide of the present invention comprises "an oligonucleotide having a sequence identical to that of a continuous stretch of 5 to 60 bases in the nucleotide sequence as described in the SEQ ID NO: 1 or 3. Such a polynucleotide has a continuous stretch of 5 to 60 bases in the nucleotide sequence as described in any one of SEQ ID NO: 1 or 3. For example, the polynucleotide is an oligonucleotide having a sequence identical to the nucleotide sequence e.g. 5, 8, 10, 12, 15, 20, 25, 30, 40, 50, and 60. The polynucleotide also comprises an oligonucleotide with the complementary sequence and their oligonucleotide derivatives. The "oligonucleotide derivatives" used herein refers to various oligonucleotide derivatives, wherein the phosphoric acid diester bond in the oligonucleotide is transformed to a phosphorothioate bond or an N3'-P5' phosphoamidate bond, the bond of ribose and phosphoric acid diester is transformed to a peptide bond, uracil in the oligonucleotide is replaced by C-5 propionyluracil or C-5 thiazole uracil, cytosine in the oligonucleotide is replaced by C-5 propionylcytosine or phenoxadine-modified cytosine, or ribose in DNA is replaced by 2'-O-propylribose and 2'-methoxyethoxyribose. Such a polynucleotide is, for example, useful as a genetic marker, a PCR primer, and a probe for hybridization.

The present invention comprises a vector comprising the polynucleotide of the present invention, the transformant transformed by the vector and a method of preparation of the polypeptide of the present invention using the transformant. Knockout animals and transgenic animals can be provided by the present invention. These modified animals are any mammals, except for human, and are preferably exemplified by rodents, such as mouse, rat, hamster, and guinea-pig.

Terms used in the present invention refer to the usual meanings in the concerned field, unless otherwise mentioned, and described below.

The term "antibody" is used according to the usual meaning in the concerned field, including the whole antibody or a fragment of the antibody, its derivative, its conjugation and its modulator. The antibody is preferably an antibody, which recognizes the polypeptide of the present invention, more preferably recognizes the polypeptide of the present invention specifically and most preferably recognizes the polypeptide only and specifically. Such an antibody may be a polyclonal or monoclonal antibody.

The "detection or quantitative analysis" of the polypeptide of the present invention is carried out using an appropriate method including immunologic methods. Such a method is exemplified by ELISA (Enzyme Linked Immuno-Sorbent Assay) method, RIA (Radio Immuno Assay) method, fluorescent antibody method, western blotting method, and immune structure dyeing method.

Cancer and/or bone disease can be detected using the antibody of the present invention. Since the polypeptide of the present invention can be a cancer marker and/or a bone disease marker, the detection can be accomplished using appropriate immunologic measuring methods as well as the above-mentioned detection or quantitative analysis of the polypeptide.

The present invention relates to a kit comprising the antibody for diagnosis of cancer or bone diseases. This kit comprises at least the antibody of the present invention and polypeptide of the present invention as a standard reagent. Since the polypeptide of the present invention is a cancer marker and/or has a BMP-binding activity, the polypeptide of the present invention can be detected immunologically, based on the above mentioned detection method of cancer and bone diseases.

The "detection or quantitative analysis" of mRNA of polypeptide of the present invention may be carried out using an appropriate mRNA detecting method including molecular biology methods. Such methods are exemplified by the Northern hybridization method, the dot blotting method, and the RT-PCR method.

Cancer and/or bone disease can be detected by the method of measuring mRNA of the present invention. Since the polypeptide of the present invention can be a cancer marker and/or a bone disease marker, the detection can be accomplished using an appropriate method including molecular biology methods such as an mRNA detection method and/or a quantitative analysis method as described above.

The present invention relates to a detection kit for cancer and/or bone diseases comprising a part or whole of a polynucleotide encoding the polypeptide of the present invention, a standard agent and a part or whole of the polynucleotide. Since the polynucleotide of the present invention can be a cancer marker or a bone disease marker, the polynucleotide can be detected by molecular biology methods based on the above mentioned detection method of cancer or bone disease.

A transcription of DNA or a translation of mRNA can be suppressed using the polynucleotide of the present invention. A suppression method of a transcription of DNA or a translation of mRNA of the polypeptide can be conducted by suitably preparing a polynucleotide, which has a complementary nucleotide sequence to the polynucleotide of the present invention or hybridizes with the polynucleotide of the present invention, an oligonucleotide having a complementary sequence to the oligonucleotide having a continuous stretch of 5 to 60 bases in the nucleotide sequence of the polynucleotide of the present invention, an oligonucleotide derivative or the like, using antisense RNA/DNA techniques that are well-known in this field.

The present invention relates to an agent that binds to the polypeptide of the present invention. The term "binding agent" herein used refers to an arbitrary agent which can bind to the polypeptide or the polynucleotide of the present invention. Such a binding agent is exemplified by a low molecular weight compound, a polynucleotide, and a polypeptide.

The "screening method of a binding agent" can be carried out by applying publicly known techniques in this field and is exemplified by bio-assay, and binding assay.

The "kit for screening of a binding agent" of the present invention comprises at least the polypeptide or the polynucleotide of the present invention or apart thereof. Screening of the above mentioned binding agent of the present invention can be carried out by the biological method using the kit.

The present invention relates to an "agent for modulating a binding activity". The term "modulating a binding activity" herein used means to increase or decrease the binding activity between the polypeptide of the present invention and the binding agent of the present invention and the "binding activity" can be evaluated by the Percent Maximum Binding (PMB). The "agent for modulating a binding activity" is an agent which increases or decreases the binding activity between the polypeptide of the present invention and a binding agent of the present invention and such an agent is exemplified by a low molecular weight compound, a polynucleotide, and a polypeptide.

The "screening method for an agent that modulates binding activity" can be achieved by applying publicly known techniques in the present field. An agent for modulating a binding activity of the present invention can be screened by the method, exemplified by bio-assay and binding-assay.

A "kit for screening for an agent that modulates binding activity" includes at least the whole or a fragment of the polypeptide and the whole or a fragment of polynucleotide of the present invention. Screening for an agent that modulates binding activity can be accomplished by biological techniques using the kit of the present invention based on the above-mentioned screening method for determining if an agent modulates binding activity.

The present invention relates also to "an agent for modulating the expression". The term "the expression" used herein means a quantitative expression of the protein or mRNA of the present invention in the target cells. The expression can be evaluated using the antibody of the present invention by measuring the protein of the present invention using an appropriate method including immunoassays e.g. ELISA, RIA, a fluorescent antibody method, and an immune structure dyeing method, or by measuring the mRNA of the polypeptide of the present invention using an appropriate method including biological measuring methods e.g. the Northern blot hybridization method, the dot blotting method, and the RT-PCR method. The term "modulating the expression" herein used means to increase or decrease the expression of the protein of the polypeptide or mRNA of the present invention which is evaluated with an appropriate method, including the above mentioned immunoassay, biological assay or the like. The term "an agent for modulating expression" used herein means an agent which increases or decreases the expression of the protein of the polypeptide or mRNA of the present invention which is evaluated by an appropriate method, including the above mentioned immunoassay, biological assay or the like and such an agent is exemplified with low molecular weight compound, polynucleotide, or polypeptide.

A "method of screening for an agent that modulates binding activity of expression" of the present invention can be accomplished by appropriately applying well-known techniques in this field. An agent that modulates binding activity can be screened by the screening method, exemplified by bioassay and binding assay.

A "kit for screening for an agent that modulates expression" includes at least the whole or a fragment of the polypeptide, the whole or a fragment of the polynucleotide or the like of the present invention. An agent that modulates expression can be screened using the kit of the present invention by the aforementioned biological screening method.

A "pharmaceutical composition" of the present invention may comprise a polypeptide, a polynucleotide, an antibody, a binding agent, an agent for modulating binding activity, or an agent for modulating expression of the present invention and can be used as a prophylactic or a remedy for a specific disease such as cancer and bone diseases.

The amino acid sequence from #-30 to #-1 is an expected signal peptide region (SP). The amino acid sequence from #20 to #327 includes five regions, which have a homology with the Cys-rich domain of Chordin (CR; Cys-rich domain) and are represented by CR1, CR2, CR3, CR4 and CR5, in order, from the amino terminal. The amino acid sequence from 331 to 655 represents a homologous region of von Willebrand factor (vWF-like domain; von Willebrand factor like region).

FIG. 2 indicates the expression level of mRNA of C0783 polypeptide in various cancer tissues and the correspondent normal tissues.

We performed Northern blot analysis in the cancer cells and the corresponding normal cells of brain, parotid, thyroid, lung, esophagus, stomach, small intestine, duodenum, rectum, colon, kidney, adrenal gland, gallbladder, lymph node, spermary, prostate gland, bladder and ureter. The relative quantity of the expression is shown, where the quantity of the expression of mRNA of C0783 polypeptide in the normal cells is taken to be 1.

Figure 3:
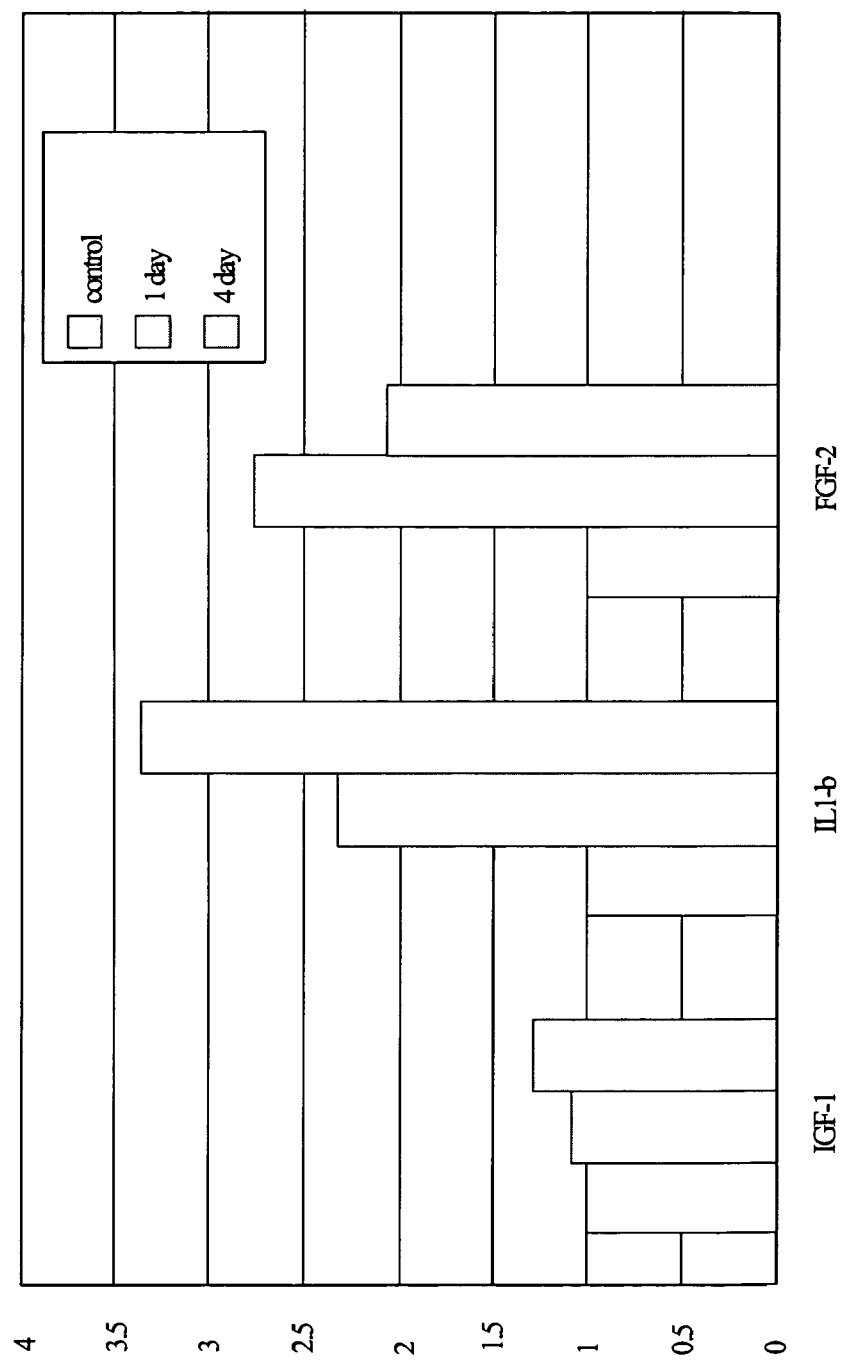

FIG. 3 indicates an alteration in the expression level of mRNA of C0783 polypeptide during bone differentiation.

We performed Northern blot analysis in human mesenchymal stem cells treated with IL-1β and EGF-2 which induce bone differentiation and IGF-1 which induces differentiation of cartilage cells. The relative quantity of the expression is shown, where the quantity of the expression of mRNA of C0783 polypeptide in control group (intact group) is taken to be 1.

Figure 4:
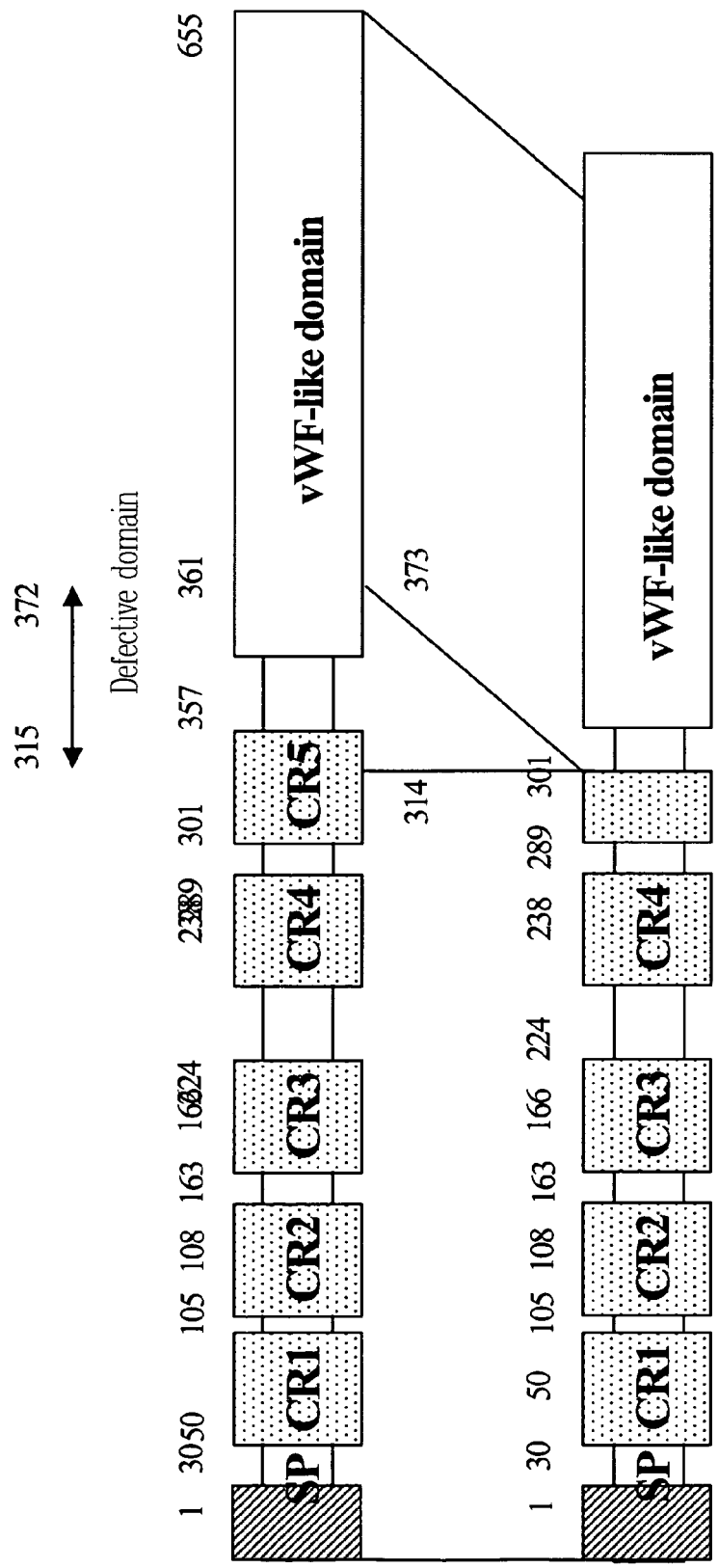

FIG. 4 indicates a scheme of the structure of C0783 deficient type of polypeptide.

Figure 1:
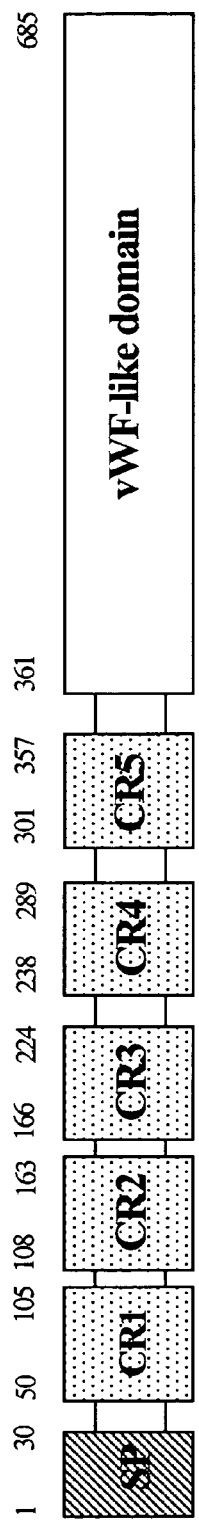
FIG. 1 indicates a scheme representing a structure of C0783 polypeptide.

The C0783 deficient type of polypeptide is a secretary protein composed of 627 amino acids. 58 amino acid residues from #315 to #372 of the C0783 polypeptide of FIG. 1 are deficient. A part of CR5, 5th Cys-rich region (Cys-rich domain 5) which is considered to be important for the function of C0783 polypeptide, and a part of von Willebrand factor-like region are deficient.

Figure 5:
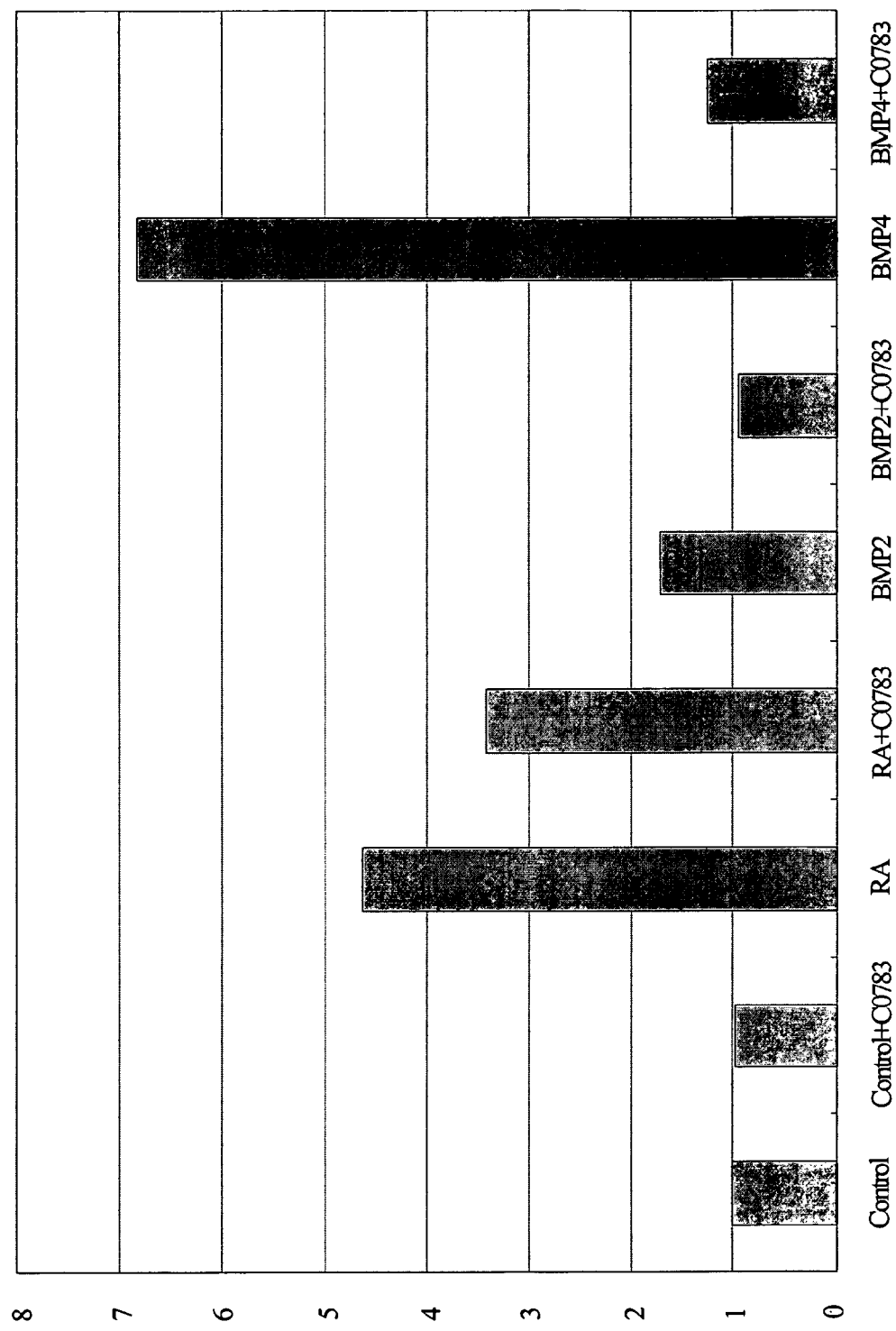

FIG. 5 indicates an inducing activity of bone differentiation of C0783 (alkaline phosphatase activity).

An alkaline phosphatase activity, a marker of bone differentiation, is used as an indicator, and an inducer of bone differentiation in the case of treatment of C0783 with BMP-2, BMP-4 and retinoic acid (RA) is shown. The relative activity is shown, when the alkaline phosphatase activity is taken to be 1 in a control (intact group).

BEST MODE FOR CARRYING OUT THE INVENTION

Explained below are methods of preparation of the polynucleotide of the present invention, methods of preparation of the polypeptide of the present invention, the recombinant vector, the transformant, the preparation method, the antibody, the quantitative analytical method of the polypeptide of the present invention, the immunological detection method, the quantitative analytical method of the mRNA, the inhibiting method of the translation of mRNA, binding agent, the screening method of the binding agent, the agent for modulating the binding activity, the screening method of the agent for modulating the binding activity, the agent for modulating expression, the screening method of the agent for modulating expression, the kit for screening, knockout animals, transgenic animals, the detection method of cancer and/or bone diseases, the kit for gene diagnosis, and the pharmaceutical composition. In the present invention, unless otherwise mentioned, a well-known technique can be used such as a gene recombination technique, a production technique of the recombinant protein in an animal cell, insect cell, yeast, Escherichia coli, or the like, an isolation and purification method of the expressed protein, an analytic method, and an immunological method.

(1) Preparation of the Polypeptide of the Present Invention

A cDNA library is produced by the usual method using human normal cells originated from human mesenchymal stem cells, brain, esophagus, stomach, lung, duodenum, ureter, intestinal cancer, colon, rectum, gallbladder, thyroid, adrenal gland, bladder and prostate gland, or using human cancer cells originated from brain, bladder, prostate gland, parotoid, lung, esophagus, stomach, duodenum, kidney, adrenal gland, ureter, spermary, small intestine and colon.

The preparation method is exemplified by the method described in Molecular Cloning: A Laboratory Manual, Second Edition (1989) (Cold Spring Harbor Laboratory Press) or Current Protocols in Molecular Biology (1994) (Green Publishing Associates and Wiley-Interscience), DNA Cloning 1: Core Techniques, A Practical Approach, Second Edition (1995) (Oxford University Press) or by the commercially available kit, e.g. Super Script Plasmid System for cDNA Synthesis and Plasmid Cloning (Invitrogen Co.) or ZAP-cDNA Synthesis Kits (STRATAGENE Co.). cDNA can be prepared using the mRNA prepared from COLO205 (ATCC:CCL-222 strain from colon glandular cancer) originated from a human cancer cell line by using a cDNA preparation kit of Super Script First-strand Synthesis System for RT-PCR (Invitrogen Co.).

After insertion of both ends of the DNA of the present invention, an EcoRI linker is inserted into a cloning vector such as e.g. pSport I (Invitrogen). A cDNA library is prepared by transformation of E. coli Electro MAX DH10B (Invitrogene Co.) using the plasmid of the present invention. A clone containing an object DNA is selected from the prepared cDNA library by the following method.

A plasmid is prepared from the cDNA library by the usual method or by using a commercially available kit, e.g. QIAGEN Plasmid Maxi Kit (Qiagen Co.).

A plasmid which has a fragment of DNA encoding an amino acid sequence homologous to chordin is selected from the above prepared cDNA library. Such a fragment of DNA can be obtained by finding two or more regions, the amino acid sequence of chordin of, which is reserved, by designing a degenerate primer corresponding to the DNA sequence encoding the amino acid sequence of the region, and by amplifying using a Polymerase Chain Reaction (PCR) method. A preparation method of the degenerate primer is exemplified by the method described in PCR Primer: A Laboratory Manual (1995) (Cold Spring Harbor Laboratory Press), The protocol series "cDNA cloning" (Jyunichiro Inoue, Kentarou Senba; Youdo Co.) and Science, 241, 42 (1988). The PCR method is exemplified by the method described in Molecular Cloning: A Laboratory Manual, Second Edition (1989) (Cold Spring Harbor Laboratory Press) and PCR Protocols (1989) (Academic Press).

The fragment of DNA amplified by the PCR method is inserted into an appropriate plasmid and then sub-cloning is accomplished. The sub-cloning can be carried out as usual by inserting the amplified DNA fragment itself or after treating it with a restriction enzyme or DNA polymerase. Such a vector is exemplified by pBluescript II SK+, pBluescript II SK−, pPCR-Script Amp (STRATAGENE Co.), pDIRECT (Nucleic Acids Research, 18, 6069 (1990), pT7Blue (Novagen Co.), pCRII (Invitrogene Co.), pCR-TRAP (Gene Hunter Co.) and pNoTAT7 (Eppendorf 5 prime Co.).

A DNA fragment encoding the amino acid sequence which is homologous but not identical with that of known chordin can be selected, by screening the sub-cloned base sequence of the PCR amplified fragment. The nucleotide sequence can be analyzed using a nucleotide sequence analyzer such as a deoxy method (Proceedings of the National Academy of Sciences USA, 74, 5463 (1977)) by Sanger et al., or a 373A DNA sequencer (Applied Biosystems Co.). By using the selected DNA fragment in this method as a probe, a cDNA encoding the polypeptide having a homology with known chordin can be obtained by hybridization analyses such as a colony hybridization, plaque hybridization or the like, to the above established cDNA library. The DNA fragment labeled by a radioisotope such as $^{32}$P, digoxigenin, an enzyme of a horseradish peroxidase or the like can be used as the probe. The hybridization can be accomplished according to the usual method described in Molecular Cloning: A Laboratory Manual, Second Edition (1989) (Cold Spring Harbor Laboratory Press).

The cDNA fragment itself, or after treated with a restriction enzyme, is inserted into a plasmid vector by the usual method, and then an objective DNA can be obtained by analyzing the nucleotide sequence using a nucleotide sequence analysis method e.g. the dideoxy method by Samger et al. (Proceedings of the National Academy of Sciences USA, 74, 5463 (1977)) or an analyzer such as a 373A DNA sequencer (Applied Biosystems Co.). The DNA encoding the polypeptide represented by the sequence of SEQ ID NO: 2 is exemplified as a DNA obtained by this method and, the DNA having a nucleotide sequence represented by the SEQ ID NO: 1. The plasmid described in an Example later is exemplified as a plasmid containing the DNA of the SEQ ID NO: 1.

An expression plasmid is constructed by inserting the obtained DNA into an appropriate expression vector, the expression vector is inserted into a suitable host and then the transformant can be prepared. The expression vector may be a vector, which can be expressed in an animal cell by inserting the cDNA. Such a vector includes, e.g., pcDNA1.1, pcDNA1.1/Amp, pCDM8, pREP (Invitrogen Co.), pHM6, pHB6 (Roche Diagnostic Co.), pKK223-3, pGEX (Amersham Pharmacia Biotech Co.), pET-3, pET-11, pBluescriptII SK(+), pBluescriptII SK(−) (STRATAGENE Co.), pUC19, pTrxFus (Invitrogen), pUC118, pSTV28 (Takara Shuzo Co.), pMAL-c2X (New England BioLabs), pAGE107 (Cytotechnology, 3(2), 133-140 (1990), JA 03-22979 A), pAGE103 (The Journal of Biochemistry, 101 (5), 1307-1310 (1987)), pAMo, pAMoA (The Journal of Biological Chemistry, 268(30), 22782-22787 (1993)), pAMoPRSA (JA 05-336963 A), pAS3-3 (JA 02-227075 A).

Any method of DNA insertion may be used as the insertion method of inserting the expression vector into a host, provided that the host is an animal cell, such as the electroporation method (Cytotechnology, 3(2), 133-140

(1990)), the phosphoric acid calcium method (JP 02-227075 A), and the lipofection method (Proceedings of the National Academy of Sciences USA, 84, 7413 (1987). Virology, 52, 456 (1973)).

The host may be an appropriate cell or tissue corresponding to the expression vector, such as animal cells, for example, cells originating from human such as Namalwa (Burkitt's lymphoma, ATCC:CRL-1432) and the sub-line Namalwa KJM-1 and HCT-15 (human colon cancer cell, ATCC:CCL-225), cells originating from monkey such as COS-1 (African green monkey nephrocyte (SV40 transformed cell), ATCC:CRL-1650) cells and COS-7 (African green monkey nephrocyte (SV40 transformed cell) and ATCC:CRL-1651) cells and cells originating from hamster, such as CHO-K1 (Chinese hamster ovarian cell, TCC:CCL-61) and HBT5637 (JA 63-299 A) cells, but preferably is the cells are Namalwa cells, Namalwa KJM-1 cells and HCT-15 cells.

The transformant of the present invention is cultured by the well-known methods. An appropriate culture medium for the transformed host cell can be used and a liquid culture is suitable for the culture of the incubation. A MEM medium culture (Science, 130, 432 (1959)), a D-MEM medium culture (Virology, 8, 396 (1959).), a RPMI1640 medium culture (The Journal of the American Medical Association, 199, 519 (1967)), a YT medium culture and a BEM medium culture are used as medium cultures. As the medium to cultivate a transformant of an animal cell, cultures which contain an appropriate amount of fetal bovine serum in a MEM medium culture, a D-MEM medium culture and a RPIM medium culture are used. If necessary, to increase the transcription activity of the promoter of the expression vector, an agent to increase the transcription activity may be added, such as, for example, isopropyl-1-thio-β-D-galactopyranosine (IPTG).

The culture medium contains essential nutriments for growing the transformant, e.g. glucose, amino acid, peptone, vitamins, hormones and serum, and preferably, FCS, Calcium Chloride and Magnesium Chloride. Such a culture medium can be any kind of composition as well as a commercially available culture medium. The incubation is carried out under a condition of pH 6.0 to 8.0, 25 to 40° C. and in the presence of 5% $CO_2$.

The desired DNA can be selected by screening the protein produced from the transformant for the ability to inhibit differentiation of the bone cell by chordin. The term "for the ability to inhibit differentiation of the bone cell" herein used refers to an activity which increases the proliferation rate of the bone cell and suppresses the transformation of the cell. The activity can be detected by the microscopic observation of the morphology of bone cells or by measurement of the differentiation marker of bone cells e.g. alkaline phosphatase (Cancer Research, 43, 4308-4314 (1983), Science, 199, 542-544 (1978)), Osteocalcine and type I collagen. To an extract made by ultrasonic disintegration of the cell, p-nitrophenylphosphate, which is a substrate of alkaline phosphatase, is added, and the mixture is incubated for an appropriate time. Then, alkaline phosphatase can be detected by quantitative measurement of p-nitrophenol e.g. using a spectrophotometer. If the activity of the alkaline phosphatase increases, then the DNA may encode a novel chordin, which relates to induction of differentiation of bone cells.

By the method mentioned above, the DNA encoding the novel polypeptide having a chordin activity, which relates to induction of differentiation of bone cells, can be obtained from a human normal cell originated from mesenchymal stem cells, brain, esophagus, stomach, lung, duodenum, ureter, intestinal cancer, colon, rectum, gallbladder thyroid, adrenal gland, bladder, prostate gland or from a human cancer cell originated from brain, bladder, prostate gland, parotid, lung, esophagus, stomach, duodenum, kidney, adrenal gland, ureter, spermary, small intestine, colon.

The DNA encodes a polypeptide, wherein the amino acid sequence may have at least one mutation selected from deletion, displacement and insertion of one or a few amino acids, compared with the amino acid sequence described in the SEQ ID NO: 2, by the selection of a DNA that hybridizes with the DNA obtained, above, under stringent conditions. That is, the objective DNA can be obtained by selecting a DNA which hybridizes under stringent conditions with a cDNA library originated from a non-human animal such as mouse, rat, cattle and monkey.

The objective DNA can also be prepared by a chemical synthesis of the DNA encoding the polypeptide based on the amino acid sequence of the screened novel chordin polypeptide. The chemical synthesis can be accomplished by a phosphoric acid triester method, a phosphoroamidate method, a phosphonic acid ester method or the like and accomplished also using a commercially available synthetic apparatus such as ABI 392 (Applied Biosystems Co.).

The objective DNA can also be prepared by PCR using a cDNA as a template that is prepared from mRNA of cells which express the complementary mRNA using an oligonucleotide mentioned later as a sense or an anti-sense primer.

(2) Preparation of the Polypeptide of the Present Invention

The polypeptide of the present invention can be prepared by expressing the polynucleotide of the present invention in a host cell using the method described in Molecular Cloning: A Laboratory Manual, Second Edition (1989) (Cold Spring Harbor Laboratory Press) or Current Protocols in Molecular Biology (1994) (Wiley-Interscience).

An appropriate length of DNA fragment containing a part encoding the polypeptide is, if necessary, prepared based on the full length of DNA encoding the polypeptide of the present invention. The part of the nucleotide sequence encoding the polypeptide is prepared so as to use suitable codons amenable to express in the host. The DNA is useful to elevate a rate of the production of the polypeptide. The DNA fragment or the full length of DNA is inserted under the control of a promoter of an appropriate expression vector and the recombinant DNA (recombinant vector) is prepared. A transformant that produces the polypeptide of the present invention can be obtained by inserting the recombinant vector into a suitable host.

Expression cells of the objective gene e.g. prokaryotes such as *Escherichia coli,* unicellular organisms such as yeast and multicellular eukaryotes such as animal cells, insect cells and plant cells, may be used as the host. Animals or plants may also be used. An expression vector may be used which has an ability of autotrophic reproduction or of insertion into a chromosome and contains a promoter at an appropriate site for the transcription of the gene of the novel chordin.

(i) Use of a Prokaryote as the Host

It is favorable that the expression vector of the novel chordin gene has autotrophic reproduction capabilities in a prokaryote and at the same time is composed of a promoter, a ribosome binding sequence, the novel chordin gene, and a transcription termination sequence. The gene may include genes controlling the promoter. The expression vector is exemplified by pHM6, pHB6 (Roche Diagnostic Co.), pKK223-3, pGEX (Amersham Pharmacia Biotech Co.), pSE280, pTrx Fus, pUC19 (Invitrogen Co.), pBluescript II SK(+), pBluescript II SK(−), pET Expression System (STRATAGEN Co.), pGEMEX-1 (Promega Co.), pQE-8 (Qiagen Co.), pMAL-c2X (New England Biolabs Co.), pKYP10 (JP 58-110600 A), pKYP200 (Agricultural Biological Chemistry, 45, 669 (1984)), pLSA1 (Agricultural Biological Chemistry, 53, 277 (1989)), pGEL1 (Proceedings of the National Academy of Sciences USA, 82, 4306 (1985)), pEG400 (Journal of Bacteriology, 172, 2392 (1990)), pTerm2 (JP 3-22979 A), pPA1 (JP 63-233798 A), pTrs30 (FERM BP-5407), pTrs32 (FERM BP-5408), pGHA2 (FERM BP-400) and pGKA2 (FERM B-6798).

The promoter may be any one that provides for expression in the host and is exemplified by a promoter originating from *Escherichia coli* or a phage, such as a trp promoter (Ptrp), a lac promoter (Plac), a Pl promoter, a Pr promoter, a PSE promoter, a SPO1 promoter, a SPO2 promoter and a penP promoter. Promoters modified artificially such as the Ptrpx2 promoter, in which Ptrp binds serially, tac promoter, lacT7 and let promoter may also be used.

It is preferable to use a plasmid in which a distance between the Shine Dalgarno (SD) sequence, a binding sequence of ribosome, and the initiation codon is controlled appropriately e.g. 6 to 18 base. The termination sequence of transcription is not always necessary for the expression of the polynucleotide of the present invention but the termination sequence of transcription preferably is located directly within the structural gene.

The host is exemplified by a prokaryote such as *Escherichia coli, Serratia, Bacillus, Brevibacterium, Corynebacterium, Microbacterium* and *Pseudomonas.* The *Escherichia coli* group is exemplified by XL1-Blue, XL2-Blue, DH1, MC1000, KY3276, W1485, JM109, HB101, No.49, W3110, NY49, BL21 (DE3), BL21 (DE3), pLysS, HMS 174 (DE3), HMS 174 (DE3) and pLysS. The *Serratia* group is exemplified by *S. ficaria, S. fonticola, S. liquefaciens* and *S. marcescens.* The *Bacillus* group is exemplified by *B. subtilis* and *B. amyloliquefaciens.* The *Brevibacterium* group is exemplified by *B. ammoniagenes, B. Immariophilum* (ATCC: 14068) and *B. saccharolyticum* (ATCC: 14066). The *Corynebacterium* group is exemplified by *C. glutamicum* (ATCC:13032), *C. glutamicum* (ATCC:14067), *C. gulutamicum* (ATCC:13869) and *C. acetoacidophilum* (ATCC:13870). The *Microbacterium* group is exemplified by *M. ammoniaphilum* (ATCC: 15354). The *Pseudomonas* group is exemplified by *S. mephitica.*

Any method of insertion of the recombinant vector may be used, provided that it is a method of inserting DNA into a host. The method is exemplified by electroporation (Nucleic Acids Research, 16, 6127 (1988)), phosphoric acid calcium. (Proceedings of the National Academy of Sciences USA, 69, 2110 (1972)), a Protoplast (JP 63-2483942 A), Gene, 17, 107 (1982) and the method described in Molecular & General Genetics, 168, 111 (1979).

(ii) Use of a Yeast as the Host

In the case of using a yeast as the host, the expression vector is exemplified by YEp13 (ATCC:37115), YEp24 (ATCC:37051), YCp50 (ATCC:37419), pHS19 and pHS15.

Any promoter may be used which expresses in the yeast and is exemplified by ADH1 (alcohol dehydrogenase), PHO5 (acidic phosphatase), PGK1 (phosphoglyceric acid kinase), GAPDH (glyceraldehyde-3-phosphoric acid dehydrogenase), GAL1 (galactose kinase) promoter, GAL10 (UDP galactose-4-epimerase), MFα1 (αpheromone) and CUP1 (metallothionine).

The host cell is exemplified by the *Saccharomyces* group, *S. cerevisiae,* the *Schizosaccharomyces* group, *S. pombe,* the *Kluyveromyces* group, *K. lactis,* the *Trichosporon* group, *T. pullulans,* the *Schwanniomyces* group, *S. alluvius,* the *Pichia* group, *P. pastoris* and the like.

Any method of insertion of the recombinant vector by which a DNA is inserted into a host may be used and is exemplified by electroporation (Methods in Enzymology, 194, 182 (1990)), spheroplast (Proceedings of the National Academy of Sciences USA, 84, 1929 (1978)), acetic acid lithium (Journal of Bacteriology, 153, 163 (1983)) and the method described in Proceedings of the National Academy of Sciences USA, 75, 1929 (1978)).

(iii) Use of an Animal Cell as the Host

In the case of using an animal cell as the host, the expression vector is exemplified by pcDNA1/Amp, pcDNA1, pCDM8, pREP4 (Invitrogen Co.), pAGE107 (Cytotechnology, 3, 133 (1990)), pAGE103 (The Journal of Biochemistry, 101, 1307 (1987)), pAMo, pAMoA (pAMo-PRSA) (The Journal of Biological Chemistry, 268, 22782-22787 (1993)) and pAS3-3 (JA 2-22705 A).

Any promoter, which promotes expression in a host, may be used. The promoter is exemplified by a promoter of the gene of IE (Imediate-early) of human cytomegalovirus (hCMV), the early promoter of SV40, the Long Terminal Repeat promoter of Moloney Murine Leukamia Virus, the promoter of retrovirus, the HSP promoter, the SR α promoter and the promoter of metallothionine. An enhancer of the IE gene of human CMV may be used with the promoter.

The animal cell used as the host is exemplified by a human cell such as HEK293 (human fetus origin nephrocyte ATCC:CRL-1573), Namalwa (Burkitt's lymphoma, ATCC: CRL-1432), HeLa (uterine neck cancer cell line, ATCC: CCL-2), HBT5637 (leukemia cell line, JA 63-299 A), BALL-1 (leukemia cell line) and HCT-15 (colon cancer cell line), by a mouse cell such as Sp2/0-Ag14 (mouse myeloma cell line, ATCC:CRL-1581) and NSO (mouse myeloma cell line), by a monkey cell such as COS-1 (African green monkey nephrocyte (SV40 transformed cell line), ATCC: CRL-1650) and COS-7 (African green monkey nephrocyte (SV40 transformed cell line), ATCC:CRL-1651), by a hamster cell such as CHO-K1 (Chinese hamster ovarian cell line, ATCC:CCL-61) and BHK-21 (C-13) (Sicilian hamster child nephrocyte, ATCC:CCL-10) or by a rat cell such as PC12 (adrenal gland pheochromocytoma, ATCC:CRL-1721) and YB2/0 (rat myeloma cell line, ATCC: CRL-1662).

Any method of inserting a recombinant vector may be used, by which a DNA can be introduced into the host, and is exemplified by electroporation (Cytotechnology, 3(2), 133-140 (1990)), phosphoric acid calcium (JP 02-227075 A), lipofection (Proceedings of the National Academy of Sciences USA, 84, 7413 (1987). Virology, 52, 456 (1973)).

(iv) Using an Insect Cell as the Host

In the case of using an insect cell as the host, the transfer vector is exemplified by pVL1392, pVL1393 and pBlue-BacIII (Invitrogen Co.). The virus to be used for infection is exemplified by a Vaculovirus which infects a Mamestra insect such as *Autographa california* nuclear polyhedrosis virus (AcMNPV) and Bac-N-Blue DNA. The method of transformation is exemplified by a method described in Baculovirus Expression Vector: A Laboratory Manual (1992) (W. H. Freeman and Company), Molecular Cloning: A Laboratory Manual, Second Edition (1989) (Cold Spring Harbor Laboratory Press), Current Protocols in Molecular Biology (1994) (Wiley-Interscience), BioTechnology, 6, 47 (1988) and thereof.

A vector including an objective gene and an infectious baculovirus DNA are transferred to an insect cell and are added to a culture medium for the insect cell, and the polypeptide can be expressed by the infection of the insect cell with the virus expressing the objective gene.

As the host, the insect cell is exemplified by one originated from *Spodoptera frugiperda*, and *Trichoplusia ni*. *Spodoptera frugiperda* are exemplified by Sf9 cells (ATCC: CRL-1711, ovarian cell) and Sf21 cells (ovarian cell). *Trichoplusia ni* cells are exemplified by High Five and BTI-TN-5B1-4 (ovum, Invitrogen Co.).

Any insertion method, by which a recombination vector can be introduced into a host, may be used and is exemplified by phosphoric acid calcium (JP 02-227075 A) and lipofection (Proceedings of the National Academy of Sciences USA, 84, 7413 (1987). Electroporation (Cytotechnology, 3(2), 133-140 (1990)) may be used in the same manner as in the case of an animal cell.

(v) Using a Plant Cell as the Host

When a plant cell is used as the host, a polypeptide can be prepared by known procedures (Tissue Culture, 20 (1994), tissue culture, 21 (1995), Trends in Biotechnology, 15, 45 (1997)). The expression vector is exemplified by Ti plasmid and the tabaco mosaic virus vector. Any promoter, which can express genes in plant cells, may be used and is exemplified by a 35S promoter of cauliflower mosaic virus (CaMV) and a rice actin 1 promoter. An efficiency of gene expression can be elevated by inserting intron 1 of the gene of alcohol dehydrogenase of cone into a site between the promoter and the expression gene.

The host may be exemplified by plant cells such as potato, tobacco, corn, rice, rape, soy bean, tomato, carrot, wheat, barley, rye, alfalfa and flax.

Any method of inserting a recombinant vector may be used, by which a DNA can be introduced into a host and is exemplified by a method using *Agrobacterium* (JP 59-140885 A, JP 60-70080 A, WO 94/00977), an electroporation method, (JP 60-251887 A), and a particle gun method (JP 2606856 C, JP 2517813 C).

(vi) Culture Method

Provided that the transformants having a recombination vector inserted with a DNA encoding the polypeptide of the present invention are cells such as *Escherichia coli*, yeast, animal cell, plant cell or the like, every host is cultured by a suitable incubation method and produces and accumulates the polypeptide. The polypeptide can be prepared by recovering the polypeptide from the transformant and/or its culture medium. Provided that the transformant is animal or plant, it grows under the suitable procedure for the host, and then it produces and accumulates the polypeptide. The polypeptide can be prepared by recovering the polypeptide from the animal and/or plant.

The host may be an animal, e.g. non-human transgenic animals wherein expression level of the polynucleotide of the present invention is raised. The polypeptide encoded by the recombinant DNA having an activity of novel chordin is produced and accumulated in the animal. The polypeptide is recovered from the animal and then the polypeptide having an activity of novel chordin can be prepared. The places of the animal, in which the polypeptide is produced and accumulated, are exemplified by milk, saliva and egg of the animal.

The host may be plant, e.g. transgenic plants having the polynucleotide of the present invention. The polypeptide encoded by the recombinant DNA having an activity of novel chordin is produced and accumulated in the plant. The polypeptide is recovered from the plant and then the polypeptide having an activity of novel chordin can be prepared.

The hosts may be prokaryotes, such as *Escherichia coli* or eukaryotes, such as yeast, e.g. the transformant having the polynucleotide of the present invention is incubated in a culture medium. The polypeptide encoded by the recombinant DNA having an activity of novel chordin is produced and accumulated in the culture medium. The polypeptide can be recovered from the culture medium and then the polypeptide having an activity of the novel chordin can be prepared.

The method of incubation of the transformant of the present invention in a culture medium may be accomplished by a typical method for the incubation of the host.

Provided that transformants are prokaryotes, such as *Escherichia coli*, or eukaryotes, such as yeast, and provided that the culture medium for incubation of the transformant includes carbon and nitrogen sources and mineral salts for host to assimilate, and that in the medium the incubation of the transformant can be accomplished effectively, any natural or synthetic culture medium may be used. The culture medium for the incubation of the transformant in which *Escherichia coli* is the host is preferably exemplified by a YT culture medium containing, Bacto Tryptone, yeast extracts and sodium chloride.

The carbon source may be a compound which can be assimilated by the host and is exemplified by glucose, fructose, sucrose, molasses, carbohydrate such as starch and its hydrolyzate, organic acid such as acetic acid and propionic acid, and alcoholic compounds such as ethanol and propanol.

The nitrogen source may be ammonia or ammonium salts of various inorganic or organic acids, such as ammonium chloride, ammonium sulfate, ammonium acetate and ammonium phosphate, or other nitrogen-containing compounds, and may be corn steep liquor, hydrolyzate of casein, soybean cake, hydrolyzate of soybean cake, fermentative cell and their digest.

The inorganic salt to be used is potassium phosphate monobasic, potassium phosphate dibasic, magnesium phosphate, magnesium sulfate, sodium chloride, iron sulfate, manganese sulfate, copper sulfate and calcium carbonate.

The incubation is carried out under an aerobic condition such as shaking or stirring with air inflation. The incubation temperature, the incubation time and the pH of the incubation medium are set up in a range suitable for the various hosts, ordinarily at 15 to 40° C., for 5 h to 7 days and in pH 3.0 to 9.0. The pH value can be controlled using inorganic or organic acid, alkaline solution, urea, calcium carbonate and ammonia. Antibiotics, such as ampicillin and tetracycline, may be added to the culture medium, if necessary. When a microorganism is cultured which is transformed by an expression vector using an inducible promoter as a promoter, an inducer may be added to the culture medium. In the case of culturing a host which is transformed by the expression vector using lac promoter or the expression vector of isopropyl-β-D-thiogalactopyranoside using a trp promoter, indoleacrylic acid may be added to the culture medium.

When the transformant is a plant cell or tissue, large-scale culture may be carried out using jar fermenters. The culture medium for incubation may be Murashige and Skoog culture medium (MS), White culture medium or that containing a plant hormone such as auxin and a cytokinine.

When the transformant is an animal cell or tissue, the culture medium for incubation may be RPMI1640 culture medium (The Journal of the American Medical Association, 199, 519 (1967)), a MEM culture medium (Science, 130, 432 (1959)), a D-MEM culture medium (Virology, 8, 396 (1959)), a 199 culture medium (Proceedings of the Society for the Biological Medicine, 73, 1 (1950)) or that containing fetal calf serum (FCS).

The incubation is ordinarily carried out in pH 6 to 8, at 25 to 40° C. and for 1 to 7 days in the presence of $CO_2$. Antibiotics, such as kanamycin, penicillin and streptomycin, may be added to the culture medium, if necessary.

When the transformant is an insect cell, the culture medium for incubation may be TNM-FH culture medium (Pharmingen Co.), Sf-900II SFM culture medium (Invitrogen Co.), an ExCell400, an ExCell405 (JRH Biosciences Co.) and a Grace's Insect Medium (Nature, 195, 788 (1962)).

(vii) Preparation Method

The polypeptide of the present invention can be prepared by culturing the transformant, and isolating and purifying the polypeptide from the culture solution. The method of isolation and purification of the polypeptide of the present invention may be well-known and is exemplified by the isolation and the purification of the enzyme or the purification method of the transglycosylation enzyme by Sandler et al. (Methods in Enzymology, 83, 458).

In the case where the polypeptide of the present invention is produced and accumulated as a soluble polypeptide, the culture medium in which the transformant is incubated is, for example, separated to the cell or fungus body and the culture medium. In the case where the polypeptide of the present invention exists in the host cell, the cell or fungus body is washed with an appropriate buffer, such as STE solution, crushed by an ultrasonic wave, French press, homogenizer, mill, followed by centrifuging and filtration to give the polypeptide as a solution without the cell.

An appropriate amount of surface active agent may be contained in the buffer used for the isolation and purification of the polypeptide of the present invention such as, for example, sodium dodecyl sulfate (SDS) and sodium N-lauroylsarcosinate.

The isolation and the purification of the objective protein included in the obtained crude product can be carried out by a combination of various kinds of known isolation and purification methods. The known methods are, for example, extraction with a solvent, salting-out or dialysis using ammonium sulfate, precipitation with an organic solvent, ultrafiltration, gel filtration, various kinds of chromatography such as diethylaminoethyl (DEAE)-sepharose chromatography, anion chromatography using Lys such as DIAION HPA-75 (Mitsubishi Chemical Co.), ion exchange chromatography, cation chromatography using Lys such as S-Sepharose FF (Pharmacia Co.), hydrophobic chromatography using butyl sepharose, affinity chromatography, electrophoresis, such as electrophoresis of SDS-polyacrylamide gel, and electrofocusing. The affinity chromatography may be conducted using the antibody raised against the polypeptide of the present invention.

In the case where the polypeptide of the present invention is produced and accumulated as an insoluble polypeptide, the cell or fungus body is isolated by the above-mentioned procedure, crushed, and the fragment of the polypeptide is recovered. The recovered sample is solubilized by a solubilizing agent such as sodium lauryl sulfate (SDS) and sodium N-lauroylsarcosinate. The solubilized solution is diluted or dialyzed to the extent that few, or no, solubilizing agent is present. After the polypeptide re-establishes the normal stereostructure, the purified specimen can be obtained according to the above isolation and purification method.

The polypeptide of the present invention may be converted to a fused protein with another protein and purified by affinity chromatography using an agent having an affinity to the fused protein (Akio Hayakawa, Experimental Medicine, 13, 469-474 (1995)). The additive protein used for the fused protein is exemplified by protein A and FLAG (Proceedings of the National Academy of Sciences USA, 86, 8227 (1989), Genes Development, 4, 1288 (1990), JP 5-536963 A, JP 6-823021 A). In the case where protein A is used, a fused protein of the polypeptide of the present invention with protein A is produced and the protein may be purified by affinity chromatography using immunoglobulin G. In the case where FLAG peptide is used, a fused protein of the polypeptide of the present invention with FLAG is produced and the protein may be purified by affinity chromatography using an antibody of anti-FLAG.

The polypeptide of the present invention may be produced using an in vitro transcription-translation system according to known procedures (Journal of Biomolecular NMR, 6, 129-134 (1995), Science, 242, 1162-1164 (1988), The Journal of Biochemistry, 110, 166-168 (1991)).

The polypeptide of the present invention may be prepared based on the amino acid sequence by a synthetic method such as the Fmoc method (fluorenylmethyloxycarbonyl method), a tBoc method (t-butyloxycarbonyl method) or using a commercially available peptide synthesis apparatus such as, APEX396 (Advanced Chem Tech Co.), 433A (Applied Biosystems Co.), PS3 (Protein Technology Co.), 9050 (Perceptive Co.) and PSSM-8 (Shimazu Co.).

The structure analysis of the polypeptide of the present invention can be achieved by known methods in protein chemistry and is exemplified by the method described in "the structure analysis of the protein for the cloning of gene" (Ed. Hisashi Hirano, published by Tokyo Kagaku Dojin 1993). The chordin-like activity of the polypeptide of the present invention may be determined according to the publicly known measuring procedure (The Journal of Biological Chemistry, 258, 9893-9898 (1983), The Journal of Biological Chemistry, 262, 15649-15658 (1987), The Journal of Biological Chemistry, 273, 58-65 (1998), The Journal of Biological Chemistry, 273, 433-440 (1998), The Journal of Biological Chemistry, 273, 12770-12778 (1998), Archives of Biochemistry and Biophysics, 270, 630-646 (1989), Archives of Biochemistry and Biophysics, 274, 14-25 (1989), JPH6-181759 A).

(3) Preparing the Transformed Polypeptide

The deletion, displacement or insertion of the amino acid of the polypeptide of the present invention may be accomplished by known methods of site-directed mutagenesis. The deletion, displacement or insertion of one or more amino acids can be prepared according to a procedure described in Molecular Cloning: A Laboratory Manual, Second Edition (1989) (Cold Spring Harbor Laboratory Press), Current Protocols in Molecular Biology (1994) (Wiley-Interscience), Nucleic Acids Research, 10, 6487 (1982), Proceedings of the National Academy of Sciences USA, 79, 6409 (1982), Gene, 34, 315 (1985), Nucleic Acids research, 13, 4431 (1985), Proceedings of the National Academy of Sciences USA, 82, 488 (1985), Proceedings of the National Academy of Sciences USA, 81, 5662 (1984), Science, 224, 1431 (1984), WO 85/00817, Nature, 316, 601 (1985).

(4) Preparation of the Antibody Recognizing the Polypeptide of the Present Invention (i) Preparation of the Polyclonal Antibody The antibody can be prepared by administering to mammals the polypeptide as an antigen, which contains the entire polypeptide or a part of the polypeptide or the polypeptide containing fragments of the polypeptide. The antigen may be bound to for instance, bovine serum albumin (BSA), keyhole limpet hemocyanin; KLH and cattle thyroglobulin (BTG). To elevate the immune reaction by the antigen, for example, a complete adjuvant (CFA) or an incomplete adjuvant (IFA) of Freund adjuvants may be administered. The mammal may be a mouse, rat, rabbit, goat and a hamster.

The polyclonal antibody can be prepared according to the procedure by Rane et al. (Antibodies: A Laboratory Manual, Second Edition (1989) (Cold Spring Harbor Laboratory Press)).

After initial administration of the antigen to the mammal, the mammal may be injected another 3 to 10 times at an interval of 1 to 2 weeks, from which the serum is collected and the polyclonal antibody can be prepared by purification.

The antigen is administered 3 to 10 times at interval of 1 to 2 weeks after the first administration. Preferably, each dose is 50 to 100 µg per body. In the case of using a peptide, the antigen is preferably covalently bound to an appropriate immunopotentiating compound. The peptide of the antigen can be prepared by a genetic engineering method or by a peptide synthesis apparatus. Blood is collected from plexus venosus of ocular fundus at 3 to 7 days after every administration so as to confirm that the serum reacts with the antigen by the enzyme immunity method of measurement (enzyme immunity method of measurement (ELISA method): published by Igakushoin (1976) and Antibodies: A Laboratory Manual, Second Edition (1989) (Cold Spring Harbor Laboratory Press).

The blood is collected from immunized mammals and the antibody titer is measured. The blood is collected at the time when sufficient antibody titer is obtained and the serum is prepared and then the polyclonal antibody can be obtained. The isolation and the purification of the polyclonal antibody is carried out by one or more of methods such as centrifugal separation, salting out with ammonium sulfate, caprylic acid precipitation (Antibodies: A Laboratory Manual, Second Edition (1989) (Cold Spring Harbor Laboratory Press) or various kinds of chromatographies such as DEAE-sepharose column, anion exchange column, protein A column and G-column gel filtration column.

(ii) Preparation of the Monoclonal Antibody (a) Preparation of the producing cell of the antibody After sufficient antibody titer is obtained in step (i), the spleen or lymph node is collected from the mammal. Then the antibody-producing cell obtained is fused with a myeloma and the monoclonal antibody producing hybridoma can be obtained. Commonly used myeloma is the cell line established from mouse or rat. The cell fusion is accomplished according to known procedures and may be carried out by the method of Kohler and Milstein (Nature, 256, 495-497 (1975)).

The spleen is collected at 3 to 7 days after an antigenic substance is administered to a rat in which the whole or a fragment of the polypeptide of the present invention or a polypeptide containing the fragment is administered to give sufficient antibody titer. The spleen is macerated in a MEM culture medium (Nissui Pharmaceuticals Co.), appeased with a dressing forceps and centrifuged at 1,200 rpm for 5 min. The obtained precipitate is treated with Tris-ammonium chloride buffer (pH 7.65) for 1 to 2 min, to remove erythrocyte, then washed with a MEM culture medium three times to give the spleen cell as an antibody-producing cell.

(b) Preparation of a myeloma

The myeloma is a mouse or rat cell line, for instance, 8-azaguanine resistance mouse (from BALB/c), P3-X63Ag8-U1 cell line (abbreviated as P3-U1 later) (Current Topics Microbiological Immunology, 81, 1 (1978), European Journal of Immunology, 6, 511 (1976)), SP2/0-Ag14 cell line (abbreviated as SP-2 later) (Nature, 276, 269 (1978)), P3-X63-Ag8653 cell line (abbreviated as 653 later) (Journal of Immunology, 123, 1548 (1979)), P3-X63-Ag8 (abbreviated as X-63 later) (Nature, 256, 495 (1975)). These cell lines are sub-cultured in a 8-azaguanine culture medium (a normal culture medium containing 15 µg/ml of 8-azaguanine (RPMI1640 culture medium containing 1.5 mM glutamine, $5 \times 10^{-5}$ M 2-mercaptoethanol, 10 µg/ml, gentamicin and 10% FCS (CSL Co.))) and cultured in a normal culture medium for 3 to 4 days before cell fusion. More than $2 \times 10^7$ of prepared cells are used.

(c) Preparation of a hybridoma

Both the antibody-producing cell line prepared in (a) and the myeloma cell line prepared in (b) are washed with a MEM culture medium or PBS (1.83 g sodium phosphate dibasic, 0.21 g potassium phosphate monobasic, 7.65 g NaCl, pH 7.2 per 1 litter), then mixed with myeloma cells so as to make the number of the antibody-producing cells 5 to 10 times greater than the myeloma cell and the mixture is centrifuged at 1,200 rpm for 5 min, to give a precipitate. The precipitate obtained is loosened well and 0.2 to 1 ml of a polyethyleneglycol solution (2 g polyethyleneglycol-1000 (PEG-1000), 2 ml MEM culture medium, 0.7 ml dimethylsulfoxide (DMSO)) are added at 37° C. with stirring per $10^8$ of the antibody-producing cells. Then, 1 to 2 ml of the MEM culture medium is added thereto a few times every 1 to 2 min. The total volume is adjusted to be 50 ml by adding the MEM culture medium. After the mixture was centrifuged at 900 rpm for 5 min, a precipitate was obtained. 100 ml of a HAT culture medium (normal culture medium containing $10^{-4}$ M hypoxanthine, $5 \times 10^{-5}$ M thymidine and $4 \times 10^{-7}$ M aminopterin) is added to the precipitate, which is loosened softly and suspended.

100 µl of the suspension is added to each well of a 96-well culture plate and incubated at 37° C. under 5% $CO_2$ for 7 to 14 days. An antibody-producing hybridoma which reacts specifically with the polypeptide of the present invention is selected from the antibody produced in the culture supernatant by an enzyme immunity method of measurement, as in, Antibodies: A Laboratory Manual, Second Edition (1989) (Cold Spring Harbor Laboratory Press)).

(5) Immunological Detection of the Polypeptide of the Present Invention

An immunological detection method of the polypeptide of the present invention is exemplified by a method of measuring the polypeptide or the fragment using a marker in which the polypeptide or the fragment is directly or indirectly bound to an enzyme, a fluorescent material, a radio-isotope, or a latex. The measuring method is exemplified by an ELISA method which is detected by an enzyme-labeling of the peroxidase of horseradish and alkaline phosphatase, a chemiluminescence method, a FITC method which detects fluorescent labeling such as luminol, GFP (Green Fluorescence Protein), a RIA method which detects a radioisotope labeling such as $^{125}$I and a latex coagulating method which binds with latex.

Such a measuring method is also exemplified by Western blotting and immune structure dyeing.

The polypeptide or the fragment of the present invention can be detected quantitatively using these methods.

(6) Quantitative Detection of mRNA

The expression level of the DNA encoding the polypeptide of the present invention can be detected quantitatively by detection of the mRNA using the oligonucleotide prepared from the polynucleotide of the present invention by Northern hybridization and RT-PCR.

In the case of measuring the mRNA using a normal or disease model animal such as mouse, rat, rabbit, sheep, pig, cattle, cat, dog and monkey, a pharmaceutical composition such as an anticancer is, if necessary, administrated and after an appropriate time, the internal organ such as blood, brain or stomach kidney or tissue is isolated, and then the cell is prepared. The mRNA is extracted from the cell by known methods and may be detected or analyzed by RT-PCR and Northern blot hybridization.

In the case of detecting quantitatively the mRNA from the transformant which expresses the polypeptide or its fragment of the present invention, the mRNA is extracted from the transformant by known methods and is detected or analyzed by RT-PCR and Northern blot hybridization.

(7) Identification of Gene Structure

At present, many gene sequences from the human chromosome having unknown functions are registered in databases. Therefore, by comparing the polynucleotide sequence of the present invention with the gene sequences of the human chromosome registered in the databases, the human chromosomal gene encoding the polypeptide of the present invention may be identified to clarify the gene structure. Provided that the sequence of the chromosomal gene which fits the cDNA sequence is registered, screening of the structure of exons or introns and of the promoter region of the chromosomal gene encoding the polypeptide of the present invention can be carried out by the comparison of the sequences between the cDNA and the chromosomal gene. The promoter region of the gene can be obtained using the polynucleotide of the present invention as a probe according to a known method (Ed. By Department of Cancer Suppression, Institute of Medical Science, The University of Tokyo, New cell technology experimental protocol, Shujyunsha (1993)).

The promoter region is exemplified by all of the region of the transformant of the gene encoding the polypeptide of the present invention in mammalian cells.

(8) Detection of Cancer

Detection of cancer or metastasis is exemplified by a sandwich ELISA which uses two antibodies which recognize an epitope other than that of the polypeptide of the present invention and one of which is directly or indirectly enzyme-labeled and by a competitive RIA which uses an antibody labeled by a radioisotope such as $^{125}$I, that recognizes the polypeptide of the present invention and the peptide. The expression of the polypeptide of the present invention increases in cancer cells of the cancer patient such as parotid cancer, lung cancer, esophagus cancer, gastric cancer, duodenal carcinoma, kidney cancer, ureteral cancer, testicular cancer, ovarian cancer, uterine cancer and leukemia and decreases in the cancer cell of the cancer patient such as intestinal cancer, rectal cancer, colon cancer, biliary cancer and thyroid cancer. Therefore, the detection method can be used for the diagnosis of parotid cancer, lung cancer, esophagus cancer, gastric cancer, duodenal carcinoma, kidney cancer, ureteral cancer, testicular cancer, ovarian cancer, uterine cancer and leukemia.

A search for a polymorphism of the gene of the present invention can be useful for the diagnosis and prediction of the prognosis of parotid cancer, lung cancer, esophagus cancer, gastric cancer, duodenal carcinoma, kidney cancer, ureteral cancer, testicular cancer, ovarian cancer, uterine cancer and leukemia.

A search for a relationship between the polymorphism of the present invention with the diseases in the internal organ in which the gene is expressed (brain, esophagus, stomach, lung, duodenum, ureter, intestinal cancer, colon, rectum, gallbladder thyroid, adrenal gland, bladder and prostate gland), is useful for the diagnosis of other diseases. The analysis of the polymorphism of the present gene can be accomplished using the information of the gene arrangement of the present gene. Concretely, the analysis of the polymorphism is achieved by a method such as Southern blotting, a direct sequence method, a PCR method and a DNA chip method (Journal of Medical Technology, 42, 1507-1517 (1998), Journal of Medical Technology, 42, 1565-1570 (1998)).

(9) Detection of Bone Disease

A detection of bone diseases is exemplified by a sandwich ELISA method which uses one of the two antibodies which recognize an epitope other than that reacting with the polypeptide of the present invention and one of which is directly or indirectly enzyme-labeled, and by a competitive RIA method which uses the antibody labeled by a radioisotope such as $^{125}$I, that recognizes the polypeptide of the present invention and the peptide. The polypeptide of the present invention can be used for diagnosis of bone diseases such as rheumatoid arthritis, arthritis deformans, and osteoporosis.

Since the expression of the polypeptide of the present invention increases when mesenchymal stem cells differentiate to bone cells, the polypeptide can be used, based on the analysis of the polymorphisms, for the diagnosis and prediction of the prognosis of bone diseases.

(10) Kit for Diagnosis

The polynucleotide of the present invention can be used for the diagnosis of cancer and bone diseases using a Northern hybridization method and a PCR method. The diagnosis of cancer and bone diseases can also be achieved by an immunological method using the antibody of the present invention. Therefore, in the case of the diagnosis using the polynucleotide, the labeled polynucleotide of the present invention is included in the kit. In the case diagnosis using the antibody, in addition to the antibody of the present invention, the polypeptide of the present invention is included as a standard antigen. The kit may include a calibration curve.

(11) Inhibition of Translation of mRNA

The production of the polypeptide of the present invention can be inhibited by administration of the polynucleotide of the present invention. It is possible to inhibit the transcription of the DNA encoding the polypeptide of the present invention and the translation of the mRNA encoding the polypeptide of the present invention.

(12) Screening for Binding Agents

The polypeptide or the fragment of the present invention is useful as an agent for searching or screening an agent that binds to the polypeptide of the present invention. The present invention provides a method of screening for an agent that binds to the polypeptide of the present invention by contacting the polypeptide, or the salt thereof, or a fragment of the peptide or the salt thereof with a test agent. A test agent is exemplified by a protein belonging to the TGF (transform growth factor) family such as BMP, a tissue extract from mammals such as human, mouse, rat pig, cattle, sheep and monkey and a cell culture supernatant thereof. These test agents are added to the polypeptide of the present invention and divided by measuring the differentiation-inducing activity of an osteoblast, to finally give a homogeneous ligand.

Concretely, the screening of a binding agent of the present invention is accomplished using the polypeptide or the fragment of the present invention or using a binding assay system comprising the expression system of the recombinant type of the polypeptide. The screening is accomplished also by measuring a cell stimulation activity, exhibited through the binding to the polypeptide of the present invention, e.g., arachidonic acid release, acetylcholine release, intracellular $Ca^{2+}$ release, intracellular cAMP production, intracellular cGMP production, inositol phosphate production, cell membrane potentiodynamic, phosphorylation of intracellular protein, activation of c-fos, acceleration and suppression activity of pH-lowering, loss of inhibition activity with alkaline phosphatase activation increase by BMP-4.

The polypeptide used for the screening of the binding agent may be any one which includes the polypeptide of the present invention and the fragment of the polypeptide of the present invention as described above, and the polypeptide which is expressed in large quantity using an animal cell is suitable. The above-mentioned expression method is used for the production of the polypeptide of the present invention, and it is preferable to be carried out by the expression of the DNA encoding the polypeptide in mammalian or insect cells. Ordinarily, a DNA fragment encoding the polypeptide includes, not limited thereto, a complementary DNA, the gene segment or synthetic DNA. To express effectively a DNA fragment encoding the polypeptide of the present invention in the host animal cell, it is preferable to insert the DNA fragment into a downstream region of a polyhedrin promoter of nuclear polyhedrosis virus (NPV) belonging to baculovirus in which the insect is a host, an SV40 promoter, a retrovirus promoter, a metallothionine promoter, a human heat shock promoter, a cytomegalovirus promoter and a SRα promoter. The quantity and quality of examination of the expressed peptide can be accomplished by known procedures and is exemplified by the method described in The Journal of Biological Chemistry, 267, 19555~19559 (1992).

Therefore, in the method of screening for binding activity of the present invention, the polypeptide or the material containing the fragment may be the polypeptide which is purified by a known method, the fragment, the cell or the cell sap which contains the polypeptide. In the method of screening for binding activity of the present invention, using the cell containing the polypeptide of the present invention, the cell may be immobilized with glutaraldehyde and formalin. The immobilization is accomplished by a known method. The cell containing the polypeptide of the present invention means the host cell which expresses the polypeptide of the present invention which includes e.g., *Escherichia coli, Bacilllus subtilis*, yeast, insect, cell and animal cell. The fraction of the cell sap means that containing the cell sap.

For the method of screening for a binding agent of the present invention, an appropriate polypeptide fragment and a labeled agent are necessary. The polypeptide fraction is preferably that of a natural polypeptide fraction or the recombinant type having an activity. The same order of the activity includes e.g., the binding activity to ligand and signal transduction activity. The labeled agent is exemplified by the protein belonging to the TGF (transforming growth factor) family such as BMP which is labeled with $^3$H, $^{125}$I, $^{14}$C or $^{35}$S.

To screen for an agent that binds to the polypeptide or the salt of the present invention, a polypeptide sample is prepared by suspending the cell or the membrane preparation of the polypeptide of the present invention in a suitable buffer for the screening. Any buffer may be used, which does not inhibit the binding of the ligand, such as a phosphate buffer of pH 4 to 10, preferably pH 6 to 8, Tris-HCl. To decrease the non-specific binding, a surfactant such as CHAPS, Tween-80 (Kao-Atlas Co.), digitonin or deoxycolate or various kinds of proteins such as bovine serum albumin and gelatin may also be added. To inhibit the decomposition of the receptor or the ligand by proteases, protease inhibitors, such as PMSF, leupeptin, E-64 (Peptide Institute Co.) and pepstatin, may be added. A test agent labeled with a certain quantity, preferably 5000 cpm to 500000 cpm, of $^3$H, $^{125}$I, $^{14}$C, $^{35}$S is incubated in a 0.01 to 10 ml solution of the polypeptide. To detect the quantity of non-specific binding (NSB), a reaction tube containing a large quantity of unlabeled test agent is used. Reaction was performed at 0° C. to 50° C., preferably 4° C. to 37° C. for 20 min. to 24 h, preferably 30 min to 3 h. After the reaction, the mixture was filtered through a glass filter and washed with an appropriate amount of the buffer. The radioactivity remaining in the glass filter is counted by a liquid scintillation counter or a γ-counter. The binding agent to the polypeptide or the salt thereof of the present invention may be selected from those test agents that have more than 0 cpm in the value of the count (B-NSB) after correction for non-specific binding (NSB).

For the method of screening an agent that binds to the polypeptide of the present invention, a cell stimulating activity via the polypeptide may be measured by well-known methods or commercially available kits such as arachidonic acid release, acetylcholine release, $Ca^{2+}$ release in cell, cAMP production in cell, cGMP production in cell, inositol phosphate production, potentiodynamics of the cell membrane, phosphorylation of the protein in cell, activation of c-fos, decrease or increase of the pH, lack of inhibition activity for increase of alkaline phosphatase by BMP-4. Concretely, the cell containing the polypeptide is incubated in multi-well-plates. The buffer is exchanged to an appropriate buffer which is not toxic to the fresh culture medium or the cell before the screening of binding agents, test agents are added, and the mixture is incubated for a certain time. The cell is extracted or the digestive liquor is recovered and the products are detected quantitatively according to each method. In the case where the detection of an agent indicates cell stimulation activity, such as arachidonic acid, is difficult owing to the catabolic enzyme, screening may be carried out by addition of the inhibitor to the catabolic enzyme. Inhibition of cAMP production may be detected when the production of cAMP has been raised by forskolin.

(13) Kit for the Screening for Binding Agents

The kit for screening for agents that bind the polypeptide of the present invention or the salt thereof, contains the polypeptide or the salt thereof of the present invention, the fragment of the polypeptide or the salt of the present invention, the cell containing the polypeptide of the present invention, and the cell sap fraction containing the polypeptide of the present invention. The kit for the screening of binding agents is exemplified as follows.

(i) Agent for the Screening of Binding Agents

As the screening solution and the cleaning solution, 0.05% of bovine serum albumin (Sigma Aldrich Co.) is added to Hank's Balanced Salt Solution (Invitrogen Co.). The solution is sterilized by filtration through a filter of 0.45 µm pore size and stored at 4° C. or prepared when used.

(a) CHO cell line expressing the polypeptide of the present invention is sub-cultured at $5\times10^5$ cells/well in a 12-well plate at 37° C., 5% $CO_2$ for 2 days.

(b) Labeled test agent

A solution of the test agent labeled with commercially available $^3H$, $^{125}I$, $^{14}C$ or $^{35}S$ is stored at 4° C. or –20° C. and diluted to 1 µM with a buffer solution for measurement when used. The slightly soluble test agent may be dissolved in dimethylformamide, DMSO and methanol.

(c) Non-labeled test agent

The same non-labeled agent as the labeled test agent is prepared in 100 to 1000 times concentration.

(ii) Method of Measurement (a) A CHO cell line expressing the polypeptide of the present invention is incubated in a 12-well tissue culture plate and is washed twice with 1 ml of the buffer of the measurement and 490 µl of the buffer of the measurement is added to each well.

(b) 5 µl of a labeled test agent is added and the mixture is reacted at room temperature for 1 h. 5 µl of a non-labeled test agent is added in the case of measurement of the level of non-specific binding.

(c) The reaction liquor is removed and the residue is washed with 1 ml of a washing solution for three times. The labeled test agent bound to the cell is dissolved in 0.2 M NaOH (containing 1% SDS) and mixed with 4 ml of scintillator A (Wako Pure Chemicals Co.).

(d) The radioactivity is measured using a scintillation counter (Beckmann Coulter Co.).

The binding agents which can bind to the polypeptide or the salt thereof of the present invention is exemplified by an agent which exists specifically in brain and lung. Examples include angiotensin, bombesin, cannabinoid, cholecystokinin, glutamine, serotonin, melatonin, neuropeptide Y, opioid, purine, vasopressin, oxytocin, PACAP, secretin, glucagon, calcitonin, adrenomedulin, somatostatin, GHRH, CRF, ACTH, GRP, PTH, VIP (vasoactive intestinal and related polypeptide), somatostatin, dopamine, motilin, amylin, bradykinin, CGRP (calcitonin gene-related peptide), leukotriene, pancreatic statin, prostaglandin, thromboxane, adenosine, adrenalin, IL-8, GROα, GROβ, GROγ, NAP-2, ENA-78, PF4, IP10, GCP-2, MCP-1, HC14, MCP-3, I-309, MIP1α, MIP-1β, and chemokines such as RANTES, endothelin, enterogastrine, histamine, neurotensin, TRH, pancreatic polypeptide, galanin, and a protein belonging to the TGF (transforming growth factor) family such as BMP.

(14) Screening for Modulating Agents of a Binding Activity

The polypeptide or the fragment of the present invention is useful as the agent for searching or screening for an agent that modulates binding activity to the polypeptide of the present invention. The method of screening for an agent that modulates the binding activity of the polypeptide of the present invention with a binding agent such as BMP-2 and BMP-4 can be effectively carried out by using bioassay systems or binding assay systems, which comprise an expression system of the polypeptide or the recombinant polypeptide. These agents include peptide, protein, a non-peptide agent, a synthetic agent and a fermentation product and are exemplified by (a) agents possessing cell stimulating activity via an agent that binds to the polypeptide of the present invention, such as arachidonic acid release, acetylcholine release, $Ca^{2+}$ release in cell, cAMP production in cell, cGMP production in cell, inositol phosphate production, potentiodynamic of cell membrane, phosphorylation of the protein in cell, activation of c-fos, agents which increase or decrease the pH, and (b) agents which increase or decrease the binding force of the binding agent with the polypeptide of the present invention.

The present invention provides a method of screening for an agent that modulates the binding activity of an agent that binds to the polypeptide of the present invention, the fragment of the peptide or the salt thereof, which comprises comparison of the binding level of binding agents between (i) the case of contacting the polypeptide, the fragment of the polypeptide or the salt thereof with the binding agent and (ii) the case of contacting the polypeptide, the fragment of the polypeptide or the salt thereof with the binding agent and the test agent.

The method of screening for an agent that modulates binding activity of the present invention comprises comparing each binding level of the polypeptide of the binding agent cases (I) and (ii) by, for example, detecting a cell stimulation activity.

The screening of a modulating agent of a binding activity that changes the binding properties of the binding agent with the polypeptide of the present invention of (a) measuring and comparing each binding level of the labeled binding agent to the polypeptide between the case of contacting the binding agent such as BMP-2 and BMP-4 with the polypeptide and the case of contacting the labeled binding agent with the test agent, (b) measuring and comparing each binding level of the labeled binding agent to the polypeptide in the cell or cell culture medium between the case of contacting the cell or cell culture medium containing the polypeptide with the labeled agent and the case of contacting the labeled binding agent with the test agent or (c) the measuring and comparing the binding level of the labeled binding agent to the polypeptide between the case of contacting the labeled binding agent with the polypeptide secreted in the cell culture medium by incubating the transformant containing the polynucleotide and the case of contacting the labeled binding agent with the test sample.

(15) Kit for Screening of Modulating Agents of a Binding Activity

The kit for performing the method of screening for an agent that modulates the binding properties of the binding agent, which binds to the polypeptide of the present invention, such as BMP-2 and BMP-4, includes the polypeptide of the present invention, the cell containing the polypeptide of the present invention and the cell culture medium containing the polypeptide of the present invention. Examples of the kit are as follows.

(i) Reagent for Screening for an Agent that Modulates Binding Activity

As the screening solution and the cleaning solution, 0.05% of bovine serum albumin (Sigma Aldrich Co.) is added to Hank's Balanced Salt Solution (Invitrogen Co.). The solution is sterilized by filtration through filters of 0.45 µm pore size and stored at 4° C. or prepared when used.

(a) Polypeptide of the present invention

A CHO cell line in which the polypeptide of the present invention is expressed is sub-cultured in a 12-well tissue culture plate at $5\times10^5$ cells/well and is incubated at 37° C. under 5% $CO_2$ for 2 days.

(b) Labeled test agents

A solution of the test agent labeled with commercially available $^3$H, $^{125}$I, $^{14}$C and $^{35}$S is stored at 4° C. or −20° C. and diluted to 1 μM with a buffer solution for measurement when used. The slightly soluble test agent may be dissolved in dimethylformamide, DMSO and methanol.

(c) Non-labeled test agent

The same non-labeled agent as the labeled test agent is prepared in 100 to 1000 times concentration.

(ii) Method of Measurement
  (a) A CHO cell line expressing the polypeptide of the present invention is incubated in a 12-well tissue culture plate and is washed twice with 1 ml of the buffer of the measurement and 490 μl of the buffer of the measurement is added to each well.
  (b) 5 μl of a labeled test agent is added and the mixture is incubated at room temperature for 1 h. 5 μl of a non-labeled test agent is added in the case of measurement of the level of non-specific binding.
  (c) The reaction liquor is removed and the residue is washed with 1 ml of a washing solution three times. The labeled test agent bound to the cell is dissolved in 0.2 M NaOH (containing 1% SDS) and mixed with 4 ml of scintillator A (Wako Pure Chemicals Co.).
  (d) The radioactivity is measured using a scintillation counter (Beckmann Coulter Co.).

(16) Screening of an Agent that Modulates Expression

The method of screening for an agent that modulates expression of the polypeptide or the fragment thereof of the present invention can be conducted using a polynucleotide of the present invention or the antibody described in (4).

The above screening can be accomplished by detecting the quantity of mRNA or protein of the polypeptide of the present invention or the fragment thereof, found in (i) blood of non-human mammals, specified organs, tissues or cells isolated from the organs and (ii) transformants.

(17) A Kit for a Method of Screening for an Agent that Modulates Expression

The kit for a method of screening for an agent that modulates expression of the polypeptide or the salt thereof of the present invention contains the polypeptide of the present invention, the cell containing the polypeptide of the present invention and the cell culture liquid containing the polypeptide of the present invention. Example of the kit for the screening of the present invention is as follows.

(18) A Kit for Screening Based on an Immunologic Quantitative Method

The quantitative method of detection of the polypeptide of the present invention is exemplified by a sandwich ELISA method using two kinds of monoclonal antibodies each having different epitopes which react with the polypeptide of the present invention in a liquid phase, by a radio-immuno assay using the polypeptide of the present invention labeled by a radioisotope such as $^{125}$I and the antibody that specifically recognizes this polypeptide. Then, in the case of diagnosis using the antibody, the polypeptide of the present invention is included as the standard antigen in addition to the antibody of the present invention. The kit may include a calibration curve.

(19) A Kit for Screening Based on Biologically Quantitative Methods

The expression level of DNA encoding the polypeptide of the present invention can be detected by measuring the level of mRNA by Northern hybridization, PCR or the like using the polynucleotide of the present invention or the oligonucleotide prepared from the polynucleotide.

Concretely, (i) a pharmaceutical composition such as an anticancer agent is administered into a normal or disease model of a non-human mammal, such as a mouse, a rat, a rabbit, a sheep, a pig, a cow, a cat, a dog and a monkey and, after a certain time, blood, specified organs such as brain, stomach and kidney, tissues, and cells isolated from the organ are obtained. The mRNA of the polypeptide of the present invention and the fragment including in the obtained cells is, for example, extracted by well-known extraction procedures, detected quantitatively by a TaqMan PCR method and can be analyzed by the well-known Northern blot technique. (ii) The transformant, which expresses the polypeptide of the present invention or the fragment thereof, is prepared according to the above method, and the mRNA of the polypeptide of the present invention or the fragment in the transformant can be detected quantitatively and analyzed. In the case of the diagnosis using polynucleotide, the kit also contains the labeled polynucleotide of the present invention.

(20) Preparation of Non-human Knock-out and Non-human Transgenic Animals

Using the vector containing the polynucleotide of the present invention, the DNA encoding the polypeptide of the present invention may be recombined with chromosomes in the embryonic stem cells of non-human mammals such as mouse, rat, rabbit, sheep, pig, cattle, cat, dog and monkey by known procedures such as homologous recombination, Nature, 326 (6110), 295 (1987), Cell, 51(3), 503 (1987) and the transformed clone can be prepared which is inactivated or displaced by optional sequences as described in Nature, 350 (6315), 243 (1991).

Using the embryonic stem cell clone thus prepared, a chimeric body composed of the embryonic stem cell clone and normal cell can be prepared by injecting the chimera into the blastcyst of a fertilized egg of a non-human animal or by an aggregated chimera method. BY crossbreeding of the chimeric body with a normal body, a body having transformed DNA encoding the polypeptide of the present invention of whole body cells and the crossbreed of the body may give a homo-body in which the transformant is introduced in both of the homologous chromosomes.

Thus, the transformation can be introduced into any site of the DNA encoding the polypeptide of the present invention a chromosome. By the introduction of the transformant by a method such as displacement, deletion or insertion of the nucleotide into a translation region of the DNA encoding the polypeptide of the present invention on the chromosome, the activity of the product can, for example, be changed.

By the similar introduction of the transformant into a controlled site of controlled expression, frequency of the expression, timing and tissue specificity can be changed. Further combination with a Cre-loxP system can control an expression time, an expression region and a level of the expression in more actively. As examples, deficiency of the objective gene in the region by using the promoter expressed in the special region of the brain (Cell, 87(7), 1317 (1996)) and deficiency of the objective gene which is specific to an organ at an objective time by using adenovirus which expresses Cre (Science, 278, 5335 (1997)) are known. Accordingly, a non-human knock out or a non-human transgenic animal can be prepared, in which the DNA encoding the polypeptide of the present invention on the chromosome controls the expression in an optional time and tissue, or in which the optional deletion, displacement or insertion exists in a translation region or an expression control region.

The non-human knock out or a non-human transgenic animal can induce various kinds of conditions of diseases caused from the polypeptide of the present invention at any time, at any level and at any site. Accordingly, the non-human knock out or a non-human transgenic animal of the present invention may be a very useful animal model in therapy or prevention of various kinds of diseases caused from the polypeptide of the present invention. Especially, they are useful as an evaluation model of the remedy, prophylactic pharmaceutical composition and thereof.

(21) A Pharmaceutical Composition

The pharmaceutical composition containing the antibody, the binding agent, the agent that modulates binding, the agent that modulates expression, can be administrated alone as a remedy, but it is preferable that the pharmaceutical composition is administered as a form of pharmaceutical preparation, which can be prepared by mixing the pharmaceutical composition with one or more pharmacologically acceptable carriers by known procedures.

Preferably, a route of administration should be used which is most effective to the therapy and exemplified by an oral administration or a parenteral administration such as oral, respiratory tract, rectum, subcutis, intramuscular and intravenous. The dosage form is exemplified by aerosol, capsule, tablet, granule, syrup, emulsion, suppository, injection, unction and tapes.

The dosage form suitable for the oral administration is exemplified by emulsion, syrup, capsule, tablet, powder and granule. A liquid dosage form such as emulsion and syrup is prepared using additive agents e.g. water, saccharide such as sucrose, sorbitol and fructose, glycols such as polyethyleneglycol and propyreneglycol, oil such as sesame oil, olive oil and soybean oil, antiseptics such as p-hydroxybenzoic acid, flavor such as strawberry flavor and peppermint. Capsule, tablet, powder and granule can be prepared using the additive agents e.g. filler such as lactose, glucose, sucrose, mannitol, disintegrator such as starch and sodium alginate, lubricant such as magnesium stearate and talc, binder such as polyvinyl alcohol, hydroxypropylcellulose and gelatin, surfactant such as fatty acid ester, and plasticizers such as glycerin.

A formulation suitable for the parenteral administration is injection, suppository and aerosol. An injection solution is, for example, prepared using carriers such as a salt solution, a glucose solution or their mixture. A suppository solution is, for example, prepared using carriers such as cocoa butter, hydrogenated lipid and carboxylic acids. Aerosol is prepared from the agent itself or using carriers which do not irritate the oral cavity and the respiratory tract mucosa of recipients and makes the absorption easy by dispersing the agent as fine particles. The carrier is exemplified by lactose and glycerin. A formulation such as an aerosol or a dry powder may be possible, by dependence of the properties of the agent and the carrier used. In a parenteral formulation, the exemplified carrier in the oral agent may be added.

The agents or the salt obtained using the screening method or screening kit of the present invention means a binding agent, a control agent of binding activity and a control agent of expression and concretely, an agent that controls (a) arachidonic acid release, acetylcholine release, intracellular $Ca^{2+}$ release, intracellular cAMP production, intracellular cGMP production, inositol phosphate production, cell membrane potentiodynamics, phosphorylation of intracellular protein, activation of c-fos, or an agent which increases or decreases pH, (b) agents which increase or decrease the binding force of the binding agent with the polypeptide of the present invention or (c) agents which increase or decrease expression of the polypeptide of the present invention.

The agents are exemplified by a low molecular weight compound, a peptide, a protein, an non-peptide agent and a synthetic agent fermentation product. These agents may be novel or known agents and may be natural or artificial agents. Since the agonist to the polypeptide of the present invention has the same kind of bioactivation as the binding agent to the polypeptide of the present invention, it is useful as a safe and low toxicity agent, responding to the activity of the binding agent. Since the antagonist to the polypeptide of the present invention can suppress the bioactivation of the binding agent to the polypeptide of the present invention, the antagonist is useful as a safe and low toxicity pharmaceutical composition, which suppresses the binding activity of the agent. The agent, which increases the binding force of the binding agent with the polypeptide of the present invention, is useful as a safe and low toxicity pharmaceutical composition which increases the bioactivation of the binding agent to the polypeptide of the present invention. The agent, which decreases the binding force of the binding agent with the polypeptide of the present invention, is useful as a safe and low toxicity pharmaceutical composition which decreases the bioactivation of the binding agent to the polypeptide of the present invention. The polypeptide of the present invention is, for example, considered to play some important roles in the cell such as the central functions as mentioned above. Accordingly, The agent that controls the expression of the polypeptide of the present invention or the peptide fragment thereof, can be used as a prevention and/or remedy of the disease which is related to the insufficiency of the polypeptide of the present invention. In the case of the use as the prevention and/or remedy of the disease which is related to the insufficiency of the polypeptide of the present invention, the agent is formulated by the usual procedure. The agent may, for example, be used orally as a sugar-coated tablet at need, a capsule, an elixir and a microcapsule, or non-orally as an injection as the form of a germ free solution in water or another pharmaceutically acceptable liquid or suspension. The formulation is, for example, prepared in a generally acceptable dosage form which is needed for the formulation procedure by mixing with a known and physiologically acceptable carrier, a flavor, a filler, a vehicle, a sterilizer, a stabilizer and a binder. The effective dose of formulations is intended to obtain an appropriate quantity within an indicated range.

The additive agent which can be mixed in a tablet and a capsule is a binder such as gelatin, corn starch, traganth and acacia, an excipient such as crystalline cellulose, a swelling agent such as corn starch, gelatin and alginic acid, a lubricant such as magnesium stearate, a sweetening agent such as saccharose, sucrose, lactose and saccharin, a flavor such as peppermint and cherry. In the case where the dosage form is a capsule, a liquid carrier such as fat and oil can be included. A germ free composition for injection is prepared according to known procedures of formulation, for example, by dissolving or suspending the active agent in a vehicle such as injectable water and a naturally occurring plant oil such as sesame oil and coconut oil. Injectable aqueous liquid is exemplified by an isotonic solution of D-sorbitol, D-mannitol and sodium chloride containing physiologic saline, dextrose or adjuvant and may be used together with an appropriate solubilizing agent such as an alcohol e.g. ethanol, propyleneglycol and polyethyleneglycol and with a nonionic surfactant such as polysorbate 80 and HCO-50. An oil solution is, for example, sesame oil and soybean oil and a solubilizing agent such as benzyl benzoate benzyl alcohol may be used together.

The above mentioned prophylactic and therapeutic agent may be mixed with a buffer such as a phosphate buffer and a sodium acetate buffer, a soothing agent such as benzalkonium chloride and procaine hydrochloride, a stabilizer such as human serum albumin and polyethyleneglycol, a preservative such as benzyl alcohol and phenol, an antioxidant, and thereof. The prepared injection liquid is usually in an appropriate ampoule. Since the formulation obtained is safe and low in toxicity, it can be administered to a mammal, such as human, rat, mouse, rabbit, sheep, pig, cattle, cat, dog and monkey. Although the dosage of the agent or the salt varies depending on a administration object, an object organ, a condition of a disease and an administration method, in the case of an oral administration, the daily dose for a patient of hypertension of 60 kg body weight can generally be about 0.1 to 100 mg, preferably about 1.0 to 50 mg, more preferably about 1.0 to 20 mg. In the case of a non-oral administration, for example, injection, the daily dose for a patient of hypertension of 60 kg body weight can generally be about 0.01 to 30 mg, preferably 0.1 to 20 mg, more preferably 0.1 to 10 mg, which is administered through an intravenous injection. In the case of other animals, the reduced dosage dependent on the body weight may be administered. Although the applied dose or the frequency of the administration is dependent on the therapeutic effect of an object, an administration method, a therapeutic period, an age, a body weight, generally the daily dose for an adult is 10 μg to 8 mg/kg.

EXAMPLES

Examples are shown below. The method of gene manipulation used is the procedure as described in Molecular Cloning: A Laboratory Manual, Second Edition (1989) (Cold Spring Harbor Laboratory Press) unless otherwise mentioned.

Example 1

Cloning of the cDNA Encoding the Novel Polypeptide (C0783) Having a Homology with Chordin Total RNA 500 μg was prepared from human mesenchymal stem cells (Bio Whittaker Co.) $5 \times 10^7$ by the use of TRIzol Reagent (Invitrogen Co.) according to the attached manual. Poly (A) RNA was prepared from the obtained total RNA by the use of QuickPrep Micro mRNA Purification Kit (Amersham Pharmacia Biotech Co.) according to the attached manual. A fragment of the cDNA for a cloning was prepared from poly (A)+RNA by the use of SuperScript Choice System (Invitrogen Co.).

The first strand cDNA was prepared from poly (A)+RNA 3 μg by the use of Oligo $(dT)_{12-18}$ primer and Super Script II RT and the second strand cDNA was prepared by the use of E. coli DNA polymerase and E. coli RNase H. After the cDNA having a blunt end was prepared by treating the obtained cDNA with T4 DNA Polymerase, EcoRI (Not I) Adapter was added at both 5' and 3' ends by the use of T4 DNA ligase. After the cDNA with the adapter was phosphorylated at the end of 5' by the use of T4 polynucleotide kinase, the fragment of cDNA of more than about 500 bp was recovered by cDNA size fraction columns. After vector plasmid pSport 1 (Invitrogen Co.) was treated with a restriction enzyme, EcoRI (TakaraBio Inc.), and phosphorylated at the 5' end by the use of T4 polynucleotide kinase, the fragment of the cDNA obtained by the use of T4 DNA Ligase was inserted. The obtained recombinant plasmid DNA is precipitated with ethanol and the precipitate was dissolved in TE buffer (10 mM Tris-HCl, pH 8.0, 1 mM EDTA) 20 μl. The transformant was prepared by insertion into Electro MAX DH10B (Invitrogen Co.) by electroporation (Nucleic Acid Research, 16, 6127 (1988)).

The transformant was incubated in S.O.C. culture medium (Invitrogen Co.) 1 ml at 37° C. for 1 h and applied to a LB agar culture medium containing 100 μg/ml ampicillin. The mixture was incubated at 37° C. overnight.

As the result, we obtained about 1 million of transformants (rate of insertion, 95%), which exhibited ampicillin-resistance, as the cDNA library.

The obtained transformants were applied to another LB agar culture medium and the mixture was incubated at 37° C. overnight. A plasmid was prepared from about 1,000 colonies by the use of QIA prep Spin Miniprep Kit (Qiagen Co.) according to the attached manual. The whole base sequence of the cDNA fragment was determined by a MegaBACE 500 DNA Analysis System (Amersham Pharmacia Biotech Co.) by the use of DYEnamic ET Dye Terminator Kit (Mega BACE) (Amersham Pharmacia Biotech Co.) according to the attached manual from the cloning cDNA library. An optimum alignment for the comparison of the amino acid sequence with chordin was accomplished by the use of a gene information processing software, GENETYX (Software Co.), by the procedure of Lipman-Pearson method (Science, 227, 1435-1441 (1985)).

As the result, we obtained a clone possessing a nucleotide sequence (SEQ ID NO: 5) encoding the amino acid sequence which was homologous but not identical with that of known chordin.

The plasmid containing cDNA fragment was digested with a restriction enzyme, EcoRI (TakaraBio Inc.), and treated with QIAquick Gel Extraction Kit (Qiagen Co.) according to an attached manual to give a cDNA fragment. The cDNA fragment, 50 ng, was labeled with $^{32}P$ with [α-$^{32}P$] dCTP (6000 Ci/mmol, 20 mCi/ml) (NENCo.) by the use of Rediprimer II DNA Labelling System (Amersham Pharmacia Biotech Co.) according to an attached manual. A colony hybridization analysis was accomplished by using the $^{32}P$ labeled cDNA fragment as a probe.

A human brain cDNA library, Human Brain (Clontech Co.) was applied to LB plates so as to be about $1 \times 10^4$ colonies in every plate and incubated at 37° C. overnight to form a colony. The colony obtained was transferred to a DNA blotting nylon membrane. Hybond-N (Amersham Pharmacia Biotech Co.). The nylon membrane was washed successively with a dissolving solution (10% SDS), denaturation solution (0.5 N NaOH, 1.5 M NaCl), neutralization solution (containing 0.5 M Tris-HCl, pH 7.0 (1.5 M NaCl)) and 2×SSC and dried. The transferred DNA was fixed on the nylon membrane by ultraviolet irradiation.

The above-prepared labeled probe was added to an ExpressHyb Hybridization Solution (BD Biosciences Clontech Co.). The nylon membrane fixed with the DNA was immersed into the solution and hybridization was accomplished at 65° C. for 16 h. After the hybridization, the nylon membrane was washed with 2×SSC (20×SSC: 3 M NaCl, 0.3 M sodium citrate, pH 7.0) at room temperature for 5 min., with 1×SSC at 50° C. for 30 min and 0.5×SSC at room temperature for 5 min and then dried. Then, after the nylon membrane was installed in an imaging plate cassette (Fuji Photo Film Co.) with an imaging plate (Fuji Photo Film Co.), autoradiography was carried out. Image analysis was accomplished by the use of an image analyzer FLA 3000 G. Colony hybridization was repeated to the colony in which the signal was detected, until the monoclone was obtained. A plasmid DNA was prepared from the monoclonal colony by the use of QIAprep Spin Miniprep Kit (Qiagen Co.) and the total base sequence was determined by the use of DYEnamic ET Dye Terminator Kit (MegaBACE) (Amersham Pharmacia Biotech Co.) by a MegaBACE 500 DNA Analysis System (Amersham Pharmacia Biotech Co.) according to an attached manual.

Thus, we obtained a cDNA containing a cDNA fragment (the SEQ ID NO: 1) encoding the polypeptide (the SEQ ID NO: 2; on and after C0783) composed of 685 amino acids. The region from Met of the 1st amino acid to Asn 30 residues upstream of the amino terminal of C0783 was an expected Signal Peptide (SP) region and there were five regions (CR1, CR2, CR3, CR4 and CR5 from the amino terminal) which had a homology with the Cys-rich domain (CR) of chordin in the region from Cys of 50 to Cys of 357. C0783 had a 20 to 31% of homology with the CR region of human chordin (FIG. 1).

Example 2

Expression of C0783 mRNA in Human Normal Organs

The plasmid containing the cDNA encoding C0783 in the obtained cDNA library in Example 1 was digested by a restriction enzyme, EcoR I (TakaraBio Inc.), and treated with QIAquick Gel Extraction Kit (Qiagen Co.) according to the attached manual to give a cDNA fragment containing C0783. The obtained cDNA fragment, 50 ng, was labeled with $^{32}$P with [α-$^{32}$P] dCTP (6000 Ci/mmol, 20 mCi/ml) (NEN Co.) by the use of a Rediprimer II DNA Labelling System (Amersham Pharmacia Biotech Co.) according to an attached manual. A northern blotting analysis was performed by the use of the obtained $^{32}$P labeled cDNA fragment as the probe.

The labeled probe obtained above was added to an Express Hyb Hybridization Solution (Clonetech Co.), and Human Poly A+ RNA Blots 12 Major Tissue Northern Blot (Qiagen Co.) was soaked in the solution. The mixture was hybridized at 65° C. for 16 h. After the hybridization, the nylon membrane was washed with 2×SSC (20×SSC: 3 M NaCl, 0.3 M sodium citrate, pH 7.0) at room temperature for 5 min., with 1×SSC at 50° C. for 30 min and 0.5×SSC at room temperature for 5 min and then dried. Then, after the nylon membrane was installed in an imaging plate cassette (Fuji Photo Film Co.) with an imaging plate (Fuji Photo Film Co.) and autoradiography was carried out, image analysis was accomplished by the use of a image analyzer FLA 3000 G.

Thus, the expression of the mRNA of C0783 is observed in size of about 3.8 kb in brain and lung.

Example 3

Expression of the C0783 mRNA in Human Cancer Organs

Differences in expression levels of C0783 gene in human cancer tissues compared to corresponding normal tissues were investigated.

The nylon membrane 48-Dot Tumor/Normal Tissue Total RNA Dot Blot (HATDt-I) (BioChain Institute, Inc.) on which total RNA extracted from 24 sets of the normal and the corresponding cancer tissues were fixed, was soaked in a hybridization buffer (0.5 M phosphate buffer, pH 7.2; 1% (w/V) BSA, 1 mmol/L EDTA, 7% (w/v) SDS). The mixture was hybridized at 65° C. for 1 h preliminarily. Then, the plasmid was prepared by the same procedure as in Example 2 and contained in C0783 cDNA, which was digested with a restriction enzyme, EcoR I (Takara Shuzo Co.), and the cDNA fragment, 50 ng, containing C0783, was labeled with $^{32}$P with [α-$^{32}$P] dCTP (6000 Ci/mmol, 20 mCi/ml) (NENCo.) by the use of a Rediprimer II DNA Labeling System (Amersham Pharmacia Biotech Co.) according to an attached manual, to give the labeled probe. The nylon membrane after the preliminary hybridization was soaked in the hybridization buffer containing the labeled probe. The mixture was hybridized at 65° C. for 16 h. After the hybridization, the nylon membrane was washed with 2×SSC (20×SSC; 3 M NaCl, 0.3 M sodium citrate, pH 7.0) at room temperature for 5 min., with 1×SSC, 0.2% SDS at 50° C. for 30 min and 0.5×SSC, 0.2% SDS at 50° C. for 30 min. and then dried. Then, after the nylon membrane was installed in an imaging plate cassette (Fuji Photo Film Co.) with an imaging plate (Fuji Photo Film Co.) and the image analysis was accomplished by the use of an image analyzer FLA 3000 G. The nylon membrane was de-hybridized and re-probed with labeled control 18S ribosome cDNA fragment. Then the analysis was carried out as described above. Tissues showing more than 0.01 in the expression ratio of C0783 to 18S ribosome were regarded as strongly expressing tissues. Normal tissues, which highly express C0783 gene, were brain, esophagus, stomach, lung, duodenum, ureter, intestine, colon, rectum, gallbladder, thyroid, adrenal gland, bladder and prostate. Cancer tissues, which highly express C0783 gene, were brain, bladder, prostate, parotid, lung, esophagus, stomach, duodenum, kidney, adrenal gland, ureter, testis, small intestine and colon (FIG. 2).

The intensity of each spot obtained with C0783 probe was standardized by an 18S-control signal and the expression ratio of tumor tissue to normal tissue were calculated.

As the results, the expression level of the C0783 gene was observed to be increased in a cancer tissue of parotid, kidney, stomach, lymph node, esophagus and ureter, and to be decreased in a cancer tissue of small intestine, rectum and colon.

Example 4

Expression of the C0783 mRNA in Human Mesenchymal Stem Cells

We analyzed alterations in the expression of the C0783 mRNA when human mesenchymal stem cells were differentiated to bone cells.

A human mesenchymal stem cell, Mesenchymal Stem Cell (Cambrex Co.), was incubated by using Human Mesenchymal Stem Cell Basal Medium (Cambrex Co.). The test samples were prepared by adding human IL-1β (R&D Systems Co.) so as to be 0.5 ng/ml of the final concentration, by adding human IGF-I (R&D Systems Co.) so as to be 10 ng/ml of the final concentration and by adding human FGF-basic (FGF-2) (R&D Systems Co.) so as to be 10 ng/ml of the final concentration to the cell culture medium. The control was prepared in additive-free condition. They were incubated at 37° C. in 5% $CO_2$ for 1 to 4 days. Cells were recovered from the culture medium and the RNA was extracted with a TRIZOL reagent (Invitrogen Co.) according to the procedure in the attached manual and all of the RNA was obtained. The total mRNA, 10 μg, obtained was fractionated by 1% agarose gel (containing 5.5% formalin) electrophoresis and was transferred to nylon membranes, Hybond-N (Amersham Pharmacia Biotech Co.). The nylon membrane was soaked in a hybridization buffer (0.5 M phosphate buffer, pH 7.2; 1% (w/V) BSA, 1 mmol/L EDTA, 7% (w/v), containing SDS). The mixture was hybridized at 65° C. for 1 h preliminarily. Then, the plasmid was prepared by the same procedure as in Example 2, containing the C0783 cDNA, and was digested by a restriction enzyme, EcoRI (Takara Shuzo Co.), and the cDNA fragment, 50 ng, containing C0783 was labeled with $^{32}$P with [$\alpha$-$^{32}$P] dCTP (6000 Ci/mmol, 20 mCi/ml) (NENCo.) by the use of Rediprimer II DNA Labeling System (Amersham Pharmacia Biotech Co.) according to an attached manual to give the labeled probe. The nylon membrane, after the preliminary hybridization, was soaked in the hybridization buffer containing the labeled probe. The mixture was hybridized at 65° C. for 16 h. After the hybridization, the nylon membrane was washed with 2×SSC (20×SSC; 3 M NaCl, 0.3 M sodium citrate, pH 7.0) at room temperature for 5 min, with 1×SSC at 50° C. for 30 min and 0.5×SSC at 50° C. for 30 min and then air-dried. Then, after the nylon membrane was installed in an imaging plate cassette (Fuji Photo Film Co.) with an imaging plate (Fuji Photo Film Co.) and autoradiography was carried out, image analysis was accomplished by the use of an image analyzer FLA 3000 G.

The intensities of each signal were measured and the ratio of the analytic results of the experimental to that of the control was calculated.

As the result, the expression level of C0783 increased in a treated segment with IL-1β and FGF-2 which had a differentiation activity of osteoblast but did not change in the treated segment with IGF-I which had a differentiation activity of cartilage (FIG. 3). Since the expression of C0783 is induced by the treatment with IL-1β and FGF-2 and is not induced by the treatment with IGF-I, C0783 is supposed to concern with the differentiation of osteoblast.

Example 5

Identification of a Transformant of C0783 Deficiency

The cDNA fragment, 50 ng, obtained in Experiment 1, containing a part of C0783, and shown by the sequence No. of the SEQ ID NO: 1, was labeled with $^{32}$P with [$\alpha$-$^{32}$P] dCTP (6000 Ci/mmol, 20 mCi/ml) (NENCo.) by the use of a Rediprimer II DNA Labelling System (Amersham Pharmacia Biotech Co.) according to an attached manual, to give the labeled probe. By the similar procedure of Example 1, the screening of the cDNA library was accomplished by using the labeled probe and the human brain cDNA library, Human Brain (Clontech Co.) by the colony hybridization method. Colony hybridization to the colony in which the signal was detected, was repeated until the monoclone was obtained. A plasmid DNA was prepared from the obtained monoclonal colony by using QIAprep Spin Miniprep Kit (Quigen Co.). The entire base sequence was determined by the use of a DYEnamic ET Dye Terminator Kit (MegaBACE) (Amersham Pharmacia Biotech Co.) by a MegaBACE 500 DNA Analysis System (Amersham Pharmacia Biotech Co.) according to an attached manual.

Thus, we isolated the cDNA clone (the SEQ ID NO: 3) encoding the amino acid sequence (the SEQ ID NO: 4), in which 58 amino acids were deleted, from Gly of 315 to Gln of 372, of the amino acid sequence of C0783 (FIG. 4). The cDNA lost the region containing CR5, which was considered to be important for the activity of C0783.

Example 6

Expression of C0783 in Cells of Mammals

A base sequence encoding 3×FLAG peptide was amplified from p3×FLAG-CMV-14 (Sigma Aldrich Co.) by PCR and cloned into the vector, pCR2.1-TOPO (Invitrogen Co.) and the resultant plasmid, pCR-FLAG was constructed.

The base sequence encoding C0783 shown by SEQ ID NO: 1 was inserted between Sal I and Not I site of pCR-FLAG. Next, we constructed the vector which contained C0783 cDNA and the base sequence encoding 3×FLAG polypeptide at the carboxy terminus.

The plasmid was digested by the restriction enzyme Xho I and was transferred to the Xho I site of the expression vector pLXSN (BD Biosciences Clontech Co.) and then the C0783 expression vector, pLXNS-C0783FLAG was constructed.

For the packaging of pLXNS-C0783 FLAG vector, HEK293 cell line (human fetal nephrocyte, ATCC: CRL-1573) was used as the host.

HEK293 cell was seeded at a concentration of 1×10$^5$ cell/well in a 35 mm, 6-well cluster, containing D-MEM culture medium, containing 10% (w/v) FCS, and cultured at 37° C., 5% CO$_2$ for 16 h. The procedure of transfection was performed as follows: 2 µg of pLXNS-C0783FLAG and 3 µl of Fugene (Roche Diagnostics) were added to the culture medium and cultured at 37° C., 5% CO$_2$ for 24 h. After that, the culture medium was exchanged and the cells were cultured at 37° C., 5% CO$_2$ for another 24 h.

We analyzed the expression of C0783 by Western blot according to the method of Laemli.

The 10 µl of culture supernatant from transformed HEK293 cells was separated by SDS-PAGE, and then electro-transferred to Immobilon-P membrane (Millipore Co.). The nylon membrane was soaked in blocking solution (PBS, pH 7.4; containing 5% (v/v) of skim milk) at room temperature for 1 h. After the nylon membrane was incubated with a solution of PBS (pH 7.4), containing 5% (v/v) skim milk and peroxidase (HRP) conjugated-anti-FLAG M2 monoclonal antibody (Sigma-Aldrich Co.) for 1 h, the membrane was washed for 10 min, three times. The nylon membrane was reacted with ECL Plus Western Blotting Detection Reagents (Amersham Pharmacia Biotech Co.) at room temperature and immediately exposed to X-ray film, X-OMAT AR (Kodak Co.) in an X-OMAT cassette (Kodak Co.) for several minutes. The culture supernatant from HEK293 cells without transformation was treated by the same procedure as mentioned above, and used as negative control.

As the result, the signal was detected at the expected size of 85 Kd and C0783 was confirmed to be a protein secreted in a culture supernatant.

Example 7

Expression in Baculovirus of C0783

Expression with recombinant baculovirus was carried out by the use of a Bac-to-Bac Baculovirus Expression System (Invitrogen Co.) according to the procedure as described in the attached manual.

pFastBac-C0783FLAG was constructed by inserting the cDNA fragment encoding C0783 in which 3×FLAG was added at the carboxy terminus, prepared in Example 6, into the XHO I site of pFastBacI plasmid. A recombinant bacmid DNA was generated by transforming the recombinant plasmid into Max Efficiency DH10Bac Competent Cells containing baculovirus genome (bacmid DNA). A recombinant bacmid DNA was transfected into Sf9 cells (ATCC: CRL-1711, ovarian cell) by the use of a Cell FECTIN Reagent and then the recombinant baculovirus was obtained. 2 ml of cell culture from the bacmid transfected Sf9 cells was infected to 50 ml of the Sf9 cells cultured at the a $1\times10^6$/ml concentration and the mixture was cultured at 28° C. for 40 h. The recombinant C0783FLAG protein was obtained in the supernatant by the centrifugation of culture medium.

The expression of C0783 FLAG was confirmed by the same method of Western blotting as described in Example 6.

10 µl of culture supernatant was separated by SDS-PAGE, and electro-transferred to Immobilon-P membrane (Millipore Co.). The nylon membrane was soaked in blocking solution (PBS, pH 7.4, containing 5% (v/v) of skim milk) at room temperature for 1 h. After the nylon membrane was incubated with a solution of PBS (pH 7.4), containing 5% (v/v) skim milk and peroxidase (HRP)-conjugated anti-FLAG M2 monoclonal antibody (Sigma-Aldrich Co.) for 1 h, the membrane was washed for 10 min, three times. The nylon membrane was reacted with ECL Plus Western Blotting Detection Reagents (Amersham Pharmacia Biotech Co.) at room temperature and immediately exposed to X-ray film, X-OMAT AR (Kodak Co.) in the X-OMAT cassette (Kodak Co.) for several minutes. The culture supernatant from SF-9 cells without infection was treated by the same procedure as mentioned above, and used as a negative control.

Thus, the signal was detected at the expected size of 85 Kd and C0783 was confirmed to be a protein secreted in the culture supernatant.

Example 8

Binding of C0783 with BMP 2 ml of cell culture medium from the baculovirus infected Sf9 cells, prepared in Example 7, was added to 50 ml of the Sf9 cells cultured at $1\times10^6$/ml concentration and the mixture was cultured at 28° C. for 40 h. Thirty microliters of Anti-FLAG M2 agarose affinity gel (Sigma-Aldrich Co.) was added to 1 ml of the supernatant, which was obtained from the cell culture medium, and the mixture was incubated at room temperature for 1 h with shaking. 1 µg of N-Terminal FLAG-BAP Protein (Sigma-Aldrich Co.) was added to and the 1 ml of the supernatant medium from uninfected Sf9 cells and was used as negative control. After the reaction, each agarose gel solution was divided into three portions and the BMP binding assay was carried out.

To the first gel portion, a 1 ml of BMP-2/PBS solution containing 0.1 µg of human BMP-2 (Qiagen Co.) and 1% (w/v) of BSA was added. To the second gel portion, 1 ml of BMP-4/PBS solution containing 0.1 µg of human BMP-4 (R&D Systems Co.) and 1% (w/v) of BSA was added. To the third gel portion, 1 ml of PBS solution containing 1% (w/v) of BSA was added. These mixtures were incubated at room temperature for 1 h with shaking, then the agarose gel was washed 6 times with 1 ml of PBS. The binding activity of C0783 with each BMP was measured by Western blot.

Each agarose gel incubated with BMP-2 was denatured with SDS, and then fractionated by a polyacrylamide gel electrophoresis. After electro-blotting to Immobilon-P membrane (Japan millipore Co.), the membrane was soaked in a blocking solution (PBS, pH 7.4) containing 5% (v/v) skim milk. After the nylon membrane was incubated with a solution of PBS (pH 7.4), containing 5% (v/v) skim milk and anti-BMP-2 sheep polyclonal antibody (Santa Cruz Biotechnology Co.) for 1 h, the membrane was washed for 10 min, three times. The membrane was reacted with 1 ml of PBS solution containing HRP-conjugated antibodies against goat IgG (Cappel Co.). After wash for 10 min×3, the resultant nylon membrane was reacted with ECL Plus Western Blotting Detection Reagents (Amersham Pharmacia Biotech Co.) at room temperature and immediately exposed to X-ray film, X-OMAT AR (Kodak Co.) in the X-OMAT cassette (Kodak Co.) for several minutes. The agarose gel reacted with BMP-4 was treated in the same manner, except using anti-human BMP4 monoclonal antibody (R&D Systems Co.) as a $1^{st}$ antibody and HRP conjugated antibody against mouse IgC (Cappel Co.), and evaluated binding activity against BMP4.

Thus, C0783 was confirmed to be protein that binds to BMP4 and BMP2.

Example 9

Inhibitory Effect of C0783 on Bone Differentiation

Since C0783 was confirmed to bind directly with BMP in Example 7, we examined the effects of C0783 on bone differentiation. BMP-2, BMP-4, retinoic acid and C0783 were used in the experiment and the enzyme activity of alkaline phosphatase, which was a differentiation marker of osteoblast, was measured to detect the bone differentiation of the cells quantitatively.

Mouse fetal cell line C3H/10T1/2 clone8 (ATCC:CCL-226) was incubated in Minimum Essential Medium (MEM) alpha Medium (1×) liquid (Invitrogen Co.) containing 10% of FCS and divided into a 24 well dish (Corning C.) so as to be $4\times10^4$ cell/well. The mixture was incubated at 37° C. for 16 h. The culture medium of the cell culture medium was changed to a Minimum Essential Medium (MEM) alpha Medium (1×) liquid (Invitrogen Co.) and the mixture was incubated at 37° C. for 6 h.

The control segment was additive-free. The test segments were various kinds of combinations of an agent with C0783, retinoic acid, retinoic acid+C0783, BMP-2, BMP-2+C0783, BMP-4, BMP-4+C0783, BMP-2 (R&D Systems Co.) was added so as to be 400 ng/ml in the final concentration, BMP-4 (R&D Systems Co.) was 200 ng/ml, retinoic acid (Sigma-Aldrich Co.) was $10^{-8}$ M and C0783 was 800 ng/ml in the final concentration. The mixture was incubated at 37° C. for 3 days. The culture medium of the cell culture medium was changed to a Minimum Essential Medium (MEM) alpha Medium (1×) liquid of the same concentration of the same test sample and the mixture was incubated at 37° C. for 3 days.

After the culture medium was removed from the above cell culture medium, a fracture solution (2 mM $MgCl_2$, 0.2% NP-40 (Visys Co.), 200 µl, and an Alkaline Phosphatase Substrate solution, 200 µl, prepared from an Alkaline Phosphatase Substrate Kit (Bio-Rad Laboratories Co.) were added to the cell culture, according to the procedure of the attached manual. The mixture was incubated at 37° C. for 30 min. A reaction stop solution (0.4N NaOH) 400 µl was added to the reaction mixture and the absorbance at 405 nm was measured by the use of plate reader Emax (Molecular Devices Co.).

Thus, the inhibition of differentiation to osteoblast by BMP-2 and BMP-4 was confirmed by addition of C0783 (FIG. 5).

INDUSTRIAL APPLICABILITY

The present invention provides a novel chordin-like polypeptide for a cancer marker, a remedy for parotid cancer, lung cancer, esophagus cancer, gastric cancer, duodenal carcinoma, kidney cancer, ureteral cancer, testicular cancer, ovarian cancer, uterine cancer, leukemia, intestinal cancer, colon cancer, rectal cancer, biliary cancer and thyroid cancer, a bone disease marker, a remedy for bone diseases for rheumatoid arthritis, arthritis deformans and osteoporosis, a polynucleotide encoding the polypeptide, a recombinant vector containing the DNA, a transformant containing the recombinant vector, a preparation method of the polypeptide, an antibody recognizing the polypeptide, a quantitative and immunological detection of the polypeptide using the antibody of the present invention, a diagnostic kit of cancer containing the antibody, a quantitative detection of mRNA of the polypeptide of the present invention, a method of screening for a ligand of the polypeptide, a method of screening for an agent that modulates the binding of the polypeptide and a ligand, a method of screening for an agent that modulates the binding between the polypeptide and BMP-2 or BMP-4, a method of screening for an agent that modulates the expression level of the polypeptide, a knockout animal, a transgenic animal, an antibody of the present invention, a ligand, an agent which changes the binding property with the ligand or a pharmaceutical composition containing an agent which modulates the expression.

The invention claimed is:

1. An isolated polypeptide or a salt thereof comprising the amino acid sequence consisting of #1 (Cys) to #655 (Arg) of the SEQ ID NO: 2.

2. The isolated polypeptide or a salt thereof according to claim 1, comprising the amino acid sequence consisting of SEQ ID NO: 2.

3. A method of preparing a polypeptide or the salt thereof, said polypeptide being selected from the group consisting of:
   (i) the amino acid sequence consisting of #1 (Cys) to #656 (Arg) of SEQ ID NO: 2, and
   (ii) the amino acid sequence consisting of SEQ ID NO: 2, wherein the method comprises:
      culturing a transformant transformed with a recombinant vector comprising a polynucleotide encoding said polypeptide; and isolating the polypeptide produced from said cultured transformant.

4. A method of detecting or quantitating a polypeptide, said polypeptide being selected from the group consisting of:
   (i) the amino acid sequence consisting of #1 (Cys) to #655 (Arg) of SEQ ID NO: 2, and
   (ii) the amino acid sequence consisting of SEQ ID NO: 2, comprising:
      contacting an antibody that specifically recognizes said polypeptide, with the polypeptide consisting of #1 (Cys) to #655 (Arg) of the SEQ ID NO: 2, or the polypeptide consisting of SEQ ID NO: 2; allowing specific binding of the antibody to the polypeptide, and detecting or quantitating the antibody bound to the polypeptide, thereby detecting and/or quantitating the polypeptide.

5. A kit comprising at least one polypeptide selected from the group consisting of:
   (i) the amino acid sequence consisting of #1 (Cys) to #655 (Arg) of SEQ ID NO: 2, and
   (ii) the amino acid sequence consisting of SEQ ID NO: 2.

* * * * *